United States Patent [19]
Koga et al.

[11] Patent Number: 5,614,633
[45] Date of Patent: Mar. 25, 1997

[54] BENZOPYRAN DERIVATIVES

[75] Inventors: Hiroshi Koga; Haruhiko Sato; Takenori Ishizawa; Hiroyuki Nabata, all of Shizuoka-ken, Japan

[73] Assignee: Chugai Seiyaku Kabushiki Kaisha, Tokyo, Japan

[21] Appl. No.: 387,745

[22] PCT Filed: Mar. 15, 1995

[86] PCT No.: PCT/JP93/01150

§ 371 Date: Feb. 17, 1995

§ 102(e) Date: Feb. 17, 1995

[87] PCT Pub. No.: WO94/04521

PCT Pub. Date: Mar. 3, 1993

[30] Foreign Application Priority Data

Aug. 17, 1992 [JP] Japan .................................. 4-217975
Apr. 15, 1993 [JP] Japan .................................. 5-088462

[51] Int. Cl.⁶ ................................................. G07D 405/04
[52] U.S. Cl. ................................. 546/282.7; 546/283.1; 549/399; 548/454; 544/240
[58] Field of Search ............................. 546/269, 282.7, 546/283.1; 514/337

[56] References Cited

FOREIGN PATENT DOCUMENTS

| | | |
|---|---|---|
| 0298452 | 1/1989 | European Pat. Off. . |
| 0314446 | 5/1989 | European Pat. Off. . |
| 0339562 | 11/1989 | European Pat. Off. . |
| 0376524 | 7/1990 | European Pat. Off. . |
| 0427606 | 5/1991 | European Pat. Off. . |
| 0477789 | 4/1992 | European Pat. Off. . |
| 2204868 | 11/1988 | United Kingdom . |

OTHER PUBLICATIONS

Buckle et al, A Novel, Potent Airway–Selective Potassium Channel Activator, Bioorganic & Medical Chemistry Letters, vol. 2, No. 9, pp. 1161–1164. 1992.

Bergmann et al, 4–Heterocyclyloxy–2H–1–Benzopyran Potassium Channel Activators, J. Med. Chem, vol. 33, pp. 2759–2767, 1990.

Bergmann et al, Synthesis and Anithypertensive Activity . . . Potassium Channel Activators, J. Med Chem., vol. 33, 492–504, 1990.

Buckle et al, Relaxant Activity of 4–Amido–3, 44–dihydro–2H–1–Benzopyran–3 ols . . . Trachealis, J. Med. Chem., vol. 33, pp. 3028–3034, 1990.

Evans et al, Synthesis and Antihypertensive of Substituted trans–4–Amino–3, . . . 3–ols, J. Med. Chem., vol. 26, pp. 1582–1589, 1983.

Ashwood et al, Synthesis and Antihypertensive Activity of 4–(Cyclic amindo) . . . Benzopyrans, J. Med. Chem., vol. 29, pp. 2194–2201, 1986.

Pinder et al. Journal of Pharmaceutical Sciencs, vol. 56, No. 8, pp. 970–973, Aug. 1967.

Topliss, Journal of Medical Chemistry, 1972, vol. 15, No. 10, pp. 1006–1010.

*Primary Examiner*—Jane Fan
*Attorney, Agent, or Firm*—Browdy and Neimark

[57] ABSTRACT

Novel benzopyran and benzoxazine derivatives represented by the general formula:

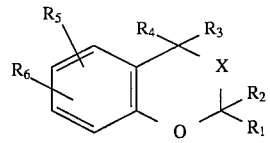

wherein $R_1$ and $R_2$ represent a lower haloalkyl group, $R_3$ represents a hydrogen atom, etc., $R_4$ represents a heterocyclic group or A—O— wherein A represents a cyclic structure, etc., $R_5$ and $R_6$ represent a lower haloalkyl, X represents =N—, N→O, etc, are disclosed. These compounds exhibit $K^+$ channel opening activating and can be widely used as an anti-asthma drug, an anti-epilepsy drug, etc.

3 Claims, No Drawings

BENZOPYRAN DERIVATIVES

This is a 371 of PCT/JP93/01150 Aug. 17, 1993 now WO94/04521.

[FIELD OF THE INVENTION]

The present invention relates to novel benzopyran and benzoxazine derivatives which are useful as medicine.

[PRIOR ART]

Hitherto, benzopyran derivatives having various pharmacological effects have been known. For example, various benzopyran derivatives in which the 4-position carbon atom of a benzopyran ring is directly linked to a nitrogen atom are disclosed in Japanese Patent Public Disclosure (Kokai) Nos. 97974/1985, 47416/1986, 165317/1988, 196581/1988, 201182/1988, 303977/1988, 26578/1989, 38087/1989, 129184/1990 and Journal of Medicinal Chemistry, vol.33, No.6, pp.1529–1541 (1990). In the above documents it is disclosed that said compounds have an anti-hypertension effect and can be used for a treatment for diseases such as heart diseases.

Among the benzopyran derivatives disclosed in the above documents, Cromakalim represented by the following formula has recently been remarked as a new kind of a hypotensive drug having an effect on $K^+$ channel together with Nicorandil and Pinacidil.

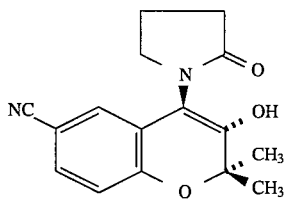

Besides, benzopyran derivatives in which the 4-position carbon atom of a benzopyran ring is not directly linked to a nitrogen atom are also disclosed in Japanese Patent Public Disclosure (Kokai) Nos.303977/1988 and 38087/1989, Official Gazette of WO90/14346, Journal of Heterocyclic Chemistry, Vol.11 (5), pp.797–802 (1974) and Journal of Medicinal Chemistry, vol.33, No.6, pp.1529–1541 (1990). Particularly, in the Official Gazette of WO90/14346 are disclosed compounds similar to the compounds of the present invention containing an amide group or a thioamide group at the 4-position of a benzopyran ring.

The present inventors have studied diligently the synthesis of a benzopyran derivative which has the equivalent or more excellent $K^+$ channel opening activities than said similar compounds and Cromakalim and in which the 4-position carbon atom of a benzopyran ring is not directly linked to a nitrogen atom and about $K^+$ channel opening activities. As a result, they have found that novel benzopyran and benzoxazine derivatives as described below, which are disclosed in no prior document, the above-mentioned pharmacological activities and accomplished the present invention on the basis of this finding.

[DISCLOSURE OF THE INVENTION]

The compounds of the present invention are novel compounds represented by the following general formula (I) having excellent $K^+$ channel opening activities.

A novel benzopyran or benzoxazine derivative represented by the general formula:

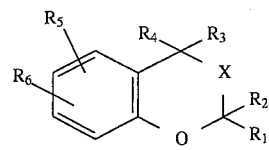

wherein $R_1$ and $R_2$, which may be the same or different, represent a lower haloalkyl group, $R_3$ represents a hydrogen atom or is directly bonded to X to represent a single bond, $R_4$ represents a substituted or unsubstituted amino group, a saturated or unsaturated heterocyclic group or A—O— wherein A represents a saturated or unsaturated carbocyclic group or a saturated or unsaturated heterocyclic group, $R_5$ and $R_6$, which may be the same or different, represent a hydrogen atom, a halogen atom, a lower alkyl group, a lower haloalkyl group, a nitro group or a cyano group, X represents =N—, $N^+$—$O^-$ or

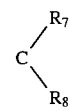

wherein $R_7$ and $R_8$, which may be the same or different, represent a hydrogen atom, a hydroxyl group or a lower acyloxy group, or $R_7$ is directly bonded to $R_3$ to represent a single bond.

In the definition of the compounds represented by the general formula (I), a lower alkyl group and an alkyl moiety in a lower haloalkyl group mean an alkyl group having 1 to 6 carbon atoms, preferably 1 to 4 carbon atoms. Examples of such a lower alkyl group include a methyl group, ethyl group, n-propyl group, i-propyl group, n-butyl group, i-butyl group, s-butyl group and t-butyl group. A halogen atom in a lower haloalkyl group means a chlorine, fluorine, bromine and iodine, preferably chlorine and fluorine. Examples of a lower haloalkyl group include a fluoromethyl group, difluoromethyl group, trifluoromethyl group, fluoroethyl group, difluoroethyl group, trifluoroethyl group and pentafluoroethyl group.

Examples of a substituent in a substituted amino group include a lower alkyl group, a lower alkanoyl group, a lower alkoxy group, and a hydroxyl group which may be protected.

Examples of a saturated or unsaturated heterocyclic group include a pyrrolidinyl group, piperidinyl group, pyridyl group, pyridadinyl group, isoindolyl group, 2-oxo-1-pyrrolidinyl group, 2-oxo-l-piperidinyl group, 2-oxo-1-pyridyl group, 2-thioxo-1-pyridyl group and 2-cyanoimino-1,2-dihydro-1-pyridyl group.

Examples of a lower acyloxy group include an acetyloxy group, propyonyloxy group, butyryloxy group and valeryloxy group.

The compound represented by the general formula (I) can be produced, for example, as follows.

The present compound can be produced by reacting a benzopyran compound represented by the general formula (II):

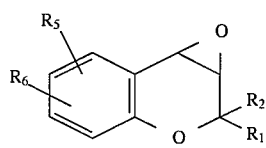

wherein $R_1$, $R_2$, $R_5$ and $R_6$ are as defined above, with a compound represented by the general formula (III):

R₄H                                    (III)

wherein $R_4$ is as defined above, in the presence of a base in an inert solvent.

Examples of a base to be used herein include sodium hydride, sodium alkoxide, potassium alkoxide, alkyl lithium, potassium carbonate, sodium carbonate, potassium hydroxide, sodium hydroxide, pyridine and triethylamine.

The compound represented by the above-mentioned general formula (I) can also be produced by acylating a compound represented by the general formula (IV):

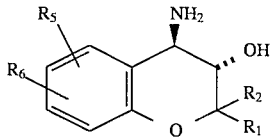

wherein $R_1$, $R_2$, $R_5$ and $R_6$ are as defined above, to give a compound represented by the general formula (V):

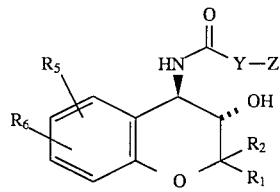

wherein Y represents a lower alkylene group, arylalkylene group, or alkylene group having a saturated or unsaturated heterocyclic group, and Z represents an elimination group such as a chlorine and a bromine, which is then subjected to cyclization in the presence of base in an inert solvent.

The compound represented by the above-mentioned general formula (I) can also be produced by reacting a compound represented by the general formula (VI):

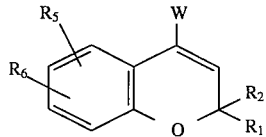

wherein W represents an elimination group such as a chlorine, bromine, methanesulfonyloxy group and trifluoromethanesulfonyloxy group, with a compound represented by the general formula (VII):

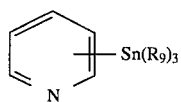

wherein $R_9$ represents a methyl group, ethyl group, n-butyl group, phenyl group, etc, in the presence of a palladium (0) complex in an inert solvent.

Examples of the palladium (0) complex used herein include a palladium (0)-phosphine complex, palladium (0)-alkene complex and palladium (0)-diene complex.

The compound represented by the above-mentioned general formula (I) can also be produced by dehydrating a compound represented by the general formula (VIII):

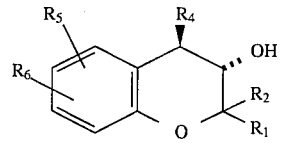

wherein $R_1$, $R_2$, $R_4$, $R_5$ and $R_6$ are as defined above.

The dehydration reaction is carried out with an acid such as paratoluenesulfonic acid and hydrogen chloride in an inert solvent, or with an acid halide such as paratoluenesulfonyl chloride, methanesulfonyl chloride and acetyl chloride or an acid anhydride such as acetic anhydride or sodium hydroxide carrier, etc, in the presence of a base. Examples of a base used herein include an organic base such as pyridine and triethylamine, and sodium hydride, sodium alkoxide, potassium alkoxide, alkyl lithium, sodium carbonate, potassium hydroxide and sodium hydroxide.

The compound represented by the above-mentioned general formula (I) can be produced by reacting a benzoxazine compound represented by the general formula (IX):

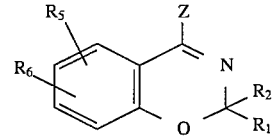

wherein $R_1$, $R_5$, $R_6$ and Z are as defined above, with a compound represented by the general formula (III) as mentioned above:

R₄H                                    (III)

wherein $R_4$ is as defined above, in the presence of a base in an inert solvent.

Examples of a base used herein include sodium hydride, sodium alkoxide, potassium alkoxide, alkyl lithium, potassium carbonate, sodium carbonate, potassium hydroxide, sodium hydroxide, pyridine and triethylamine.

Furthermore, the compound represented by the general formula (I) of the present invention can also be obtained according to the concrete methods for production as described in Examples.

Hereinafter, the production of the compound of the present invention will be explained more in detail in the Examples. The present invention is not restricted to these Examples.

EXAMPLE 1

6-Pentafluoroethyl-2,2-bisfluoromethyl-4-(2-oxo-1-pyrrolidinyl)-2H-1-benzopyran (Compound 1-1),
Trans-6-pentafluoroethyl-2,2-bisfluoromethyl-3,4-dihydro-4-(2-oxo-1-pyrrolidinyl)-2H-1-benzopyran-3-ol (Compound 1-2)

To a mixture of 0.41 g of 3,4-epoxy-6-pentafluoroethyl-2,2-bisfluoromethyl-3,4-dihydro-2H-1-benzopyran, 0.18 g of 2-pyrrolidinone and 8 ml of tetrahydrofuran was added 0.22 g of potassium tert-butoxide with stirring under ice-cooling and the mixture was stirred for 3.5 hours under ice-cooling and then stirred at room temperature for 4 days.

Water was added and the mixture was extracted with methylene chloride. After the organic layer was washed with water and dried, the solvent was distilled off. The resultant residue was purified using silica gel column chromatography (developing solution, MeOH:CH$_2$Cl$_2$=1:99) to obtain from the first eluted fraction 0.08 g of 6-pentafluoroethyl-2,2-bisfluoromethyl-4-(2-oxo-1-pyrrolidinyl)-2H-1-benzopyran represented by the following formula having a melting point of 104°–105° C.

NMR (CDCl$_3$)δ: 1.90–2.80(4H,m), 3.61(2H,t), 4.58(2H, d), 4.60(2H, d ), 5.67(1H,s), 7.01(1H,d), 7.15(1H,d), 7.46(1H,dd).

MS m/z: 397(M$^+$)

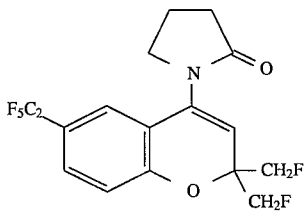

From the following eluted fraction, 0.25 g of trans-6-pentafluoroethyl-2,2-bisfluoromethyl-3,4-dihydro-4-(2-oxo-1-pyrrolidinyl)-2H-1-benzopyran-3-ol represented by the following formula having a melting point of 196°–197° C. was obtained.

NMR(CDCl$_3$)δ: 1.72–2.80(4H, m), 2.80–3.54(2H,m), 4.00–4.36(1H,m), 4.76(4H,d), 4.77(1H,d), 5.47(1H,d), 7.07(1H,d), 7.15 (1H, brs), 7.49 (1H, brd).

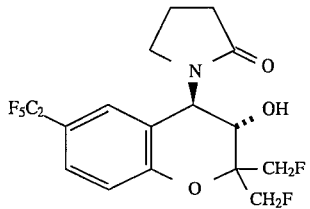

EXAMPLE 2

6-Cyano-2,2-bisfluoromethyl-4-(2-oxo-1-pyrrolidinyl)-2H-1-benzopyran, (Compound 2-1)
Trans-6-cyano-2,2-bisfluoromethyl-3,4-dihydro-4-(2-oxo-1-pyrrolidinyl)-2H-1-benzopyran-3-ol (Compound 2-2)

As a lower polarity component, 6-cyano-2,2-bis-fluoromethyl-4-(2-oxo-1-pyrrolidinyl)-2H-1-benzopyran represented by the following formula having a melting point of 140°–141° C. was obtained according to the same method as in Example 1.

NMR(CDCl$_3$)δ: 1.85–2.75(4H,m), 3.61(2H,t), 4.52(4H, d), 5.60(1H,s), 6.88(1H,d), 7.19(1H,d), 7.38(1H,dd).

MS m/z: 304(M$^+$)

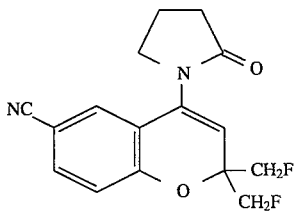

Then, as a higher polarity component, trans-6-cyano-2,2-bisfluoromethyl-3,4-dihydro-4-(2-oxo-1-pyrrolidinyl)-2H-1-benzopyran-3-ol represented by the following formula having a melting point of 216°–218° C. was obtained.

200 MHz-NMR(CDCl$_3$)δ: 2.01–2.21(1H,m), 2.50–2.64(2H,m), 2.99–3.16(1H,m), 3.24–3.43(1H,m), 3.97(1H,d), 4.21(1H,dd), 4.50–4.99(4H,m), 5.40(1H,d), 7.01(1H,d), 7.21(1H,d), 7.49(1H,dd).

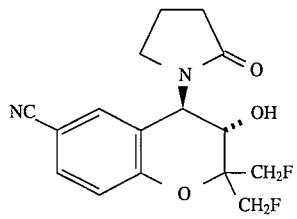

EXAMPLE 3

2,2-Bisfluoromethyl-6-nitro-4-(2-oxo-1-pyrrolidinyl)-2H-1-benzopyran (Compound 3-1),
Trans-2,2-bisfluoromethyl-3,4-dihydro-6-nitro-4-(2-oxo-1-pyrrolidinyl)-2H-1-benzopyran-3-ol (Compound 3-2)

As a lower polarity component, 2,2-bisfluoromethyl-6-nitro-4-(2-oxo-1-pyrrolidinyl)-1H-1-benzopyran represented by the following formula having a melting point of 147°–148° C. was obtained according to the same method as in Example 1.

NMR(CDCl$_3$)δ: 2.00–2.90(4H,m), 3.71(2H,t), 4.62(4H, d), 5.72(1H,s), 7.01(1H,d), 7.88(1H,d), 8.12 (1H,dd).

MS m/z: 324(M$^+$)

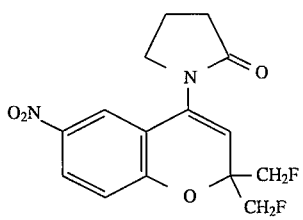

Then, as a higher polarity component, trans-2,2-bisfluoromethyl-3,4-dihydro-6-nitro-4-(2-oxo-1-pyrrolidinyl)-2H-1-benzopyran-3-ol represented by the following formula having a melting point of 256°–258° C. was obtained.

NMR(CDCl$_3$-DMSO-d$_6$)67 : 1.90–2.70(4H,m), 2.90–3.70(2H,m), 4.00–4.60(1H,m), 4.77(4H,d), 5.00–5.50(1H,m), 6.28(1H,d), 7.09(1H,d), 7.77(1H,d), 8.12(1H, dd).

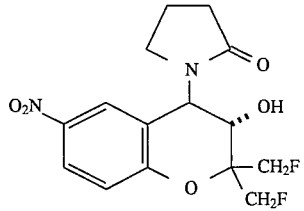

EXAMPLE 4

6-Pentafluoroethyl-2,2-bisfluoromethyl-4-(2-oxo-1-piperidinyl)-2H-1-benzopyran (Compound 4-1),
Trans-6-pentafluoroethyl-2,2-bisfluoromethyl-3,4-dihydro-4-(2-oxo-1-piperidinyl)-2H-1-benzopyran-3-ol (Compound 4-2)

To a mixture of 0.54 g of 3,4-epoxy-6-pentafluoroethyl-2,2-bisfluoromethyl-3,4-dihydro-2H-1-benzopyran, 0.24 g of 2-piperidinone and 10 ml of tetrahydrofuran was added 0.27 g of potassium tert-butoxide with stirring under ice-cooling. The mixture was stirred for 6 hours under ice-cooling and then stirred at room temperature for 16 hours. Ice water was added to the mixture, which was then extracted with methylene chloride. After the organic layer was washed with water and dried, the solvent was distilled off. The resultant residue was purified using silica gel column chromatography (developing solution, MeOH:CH$_2$Cl$_2$=1:99) to obtain from the first eluted fraction 0.02 g of 6-pentafluoroethyl-2,2-bisfluoromethyl-4-(2-oxo-1-piperidinyl)-2H-1-benzopyran represented by the following formula having a melting point of 149°–150° C.

NMR(CDCl$_3$)δ: 1.62–2.28(4H,m), 2.28–2.85(2H,m), 3.29–3.75(2H,m), 4.63(4H,brd), 5.69(1H, s), 7.03(1H,d), 7.12(1H,d), 7.48(1H,dd).

MS m/z: 411(M$^+$)

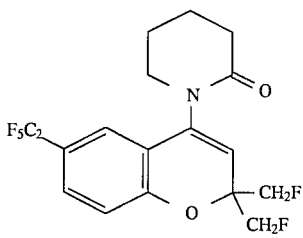

From the following eluted fraction, 0.44 g of trans-6-pentafluoroethyl-2,2-bisfluoromethyl-3,4-dihydro-4-(2-oxo-1-piperidinyl)-2H-1-benzopyran-3-ol represented by the following formula having a melting point of 199°–200° C. was obtained.

NMR(CDCl$_3$)δ: 1.60–2.10(4H,m), 2.33–2.76(2H,m), 2.76–3.40(2H,m), 3.99–4.34(1H,m), 4.72(4H,brd), 4.83(1H, d), 5.99(1H,brd), 6.99(1H,d), 7.08(1H,brs), 7.38(1H,brd).

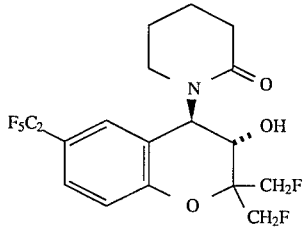

EXAMPLE 5

6-Cyano-2,2-bisfluoromethyl-4-(2-oxo-1-piperidinyl)-2H-1-benzopyran (Compound 5-1),
Trans-6-cyano-2,2-bisfluoromethyl-3,4-dihydro-4-(2-oxo-1-piperidinyl)-2H-1-benzopyran-3-ol (Compound 5-2)

As a lower polarity component, 6-cyano-2,2-bisfluoromethyl-4-(2-oxo-1-piperidinyl )-2H-1-benzopyran represented by the following formula having a melting point of 174°–176° C. was obtained according to the same method as in Example 4.

NMR (CDCl$_3$)δ: 1.73–2.23(4H,m), 2.30–2.76(2H,m), 3.25–3.74(2H,m), 4.76(4H,d), 5.63(1H,s), 6.89(1H,d), 7.11(1H,d), 7.41(1H,dd).

MS m/z: 318(M$^+$)

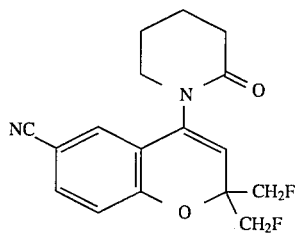

Then, as a higher polarity component, trans-6-cyano-2,2-bisfluoromethyl-3,4-dihydro-4-(2-oxo-1-piperidinyl)-2H-1-benzopyran-3-ol represented by the following formula having a melting point of 201°–203° C. was obtained.

200 MHz-NMR(CDCl$_3$)δ: 1.66–2.00(4H,m), 2.44–2.75(2H,m), 2.76–3.28(2H,m), 4.12–4.42(2H,m), 4.49–4.92(4H,m), 5.01(1H,d), 7.01(1H,d), 7.25(1H,d), 7.45(1H,dd).

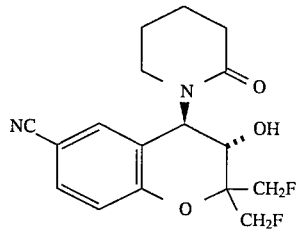

EXAMPLE 6

2,2-Bisfluoromethyl-6-nitro-4-(2-oxo-1-piperidinyl)-2H-1-benzopyran (Compound 6-1),
Trans-2,2-bisfluoromethyl-3,4-dihydro-6-nitro-4-(2-oxo-1-piperidinyl)-2H-1-benzopyran-3-ol (Compound 6-2)

As a lower polarity component, 2,2-bisfluoromethyl-6-nitro-4-(2-oxo-1-piperidinyl)-2H-1-benzopyran represented by the following formula having a melting point of 161°–162° C. was obtained according to the same method as in Example 4.

NMR(CDCl$_3$)δ: 1.70–2.30(4H,m), 2.40–2.80(2H,m), 3.40–3.70(2H,m), 4.64(4H,d), 5.72(1H,s), 6.98(1H,d), 7.77(1H,d), 8.08(1H,dd).

MS m/z: 338(M$^+$)

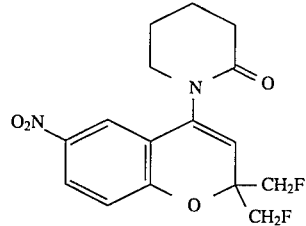

Then, as a higher polarity component, trans-2,2-bisfluoromethyl-3,4-dihydro-6-nitro-4-(2-oxo-1-piperidinyl)-2H-1-benzopyran-3-ol represented by the following formula having a melting point of 231°–233° C. was obtained.

NMR(CDCl$_3$)δ: 1.60–2.10(4H,m), 2.30–2.70(2H,m), 2.80–3.20(2H,m), 4.00–4.80(2H,m), 4.68(4H,d), 5.95(1H, brs ), 6.97(1H,d), 7.78(1H,d), 8.02(1H,dd).

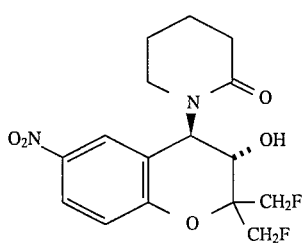

EXAMPLE 7

Trans-6-pentafluoroethyl-2,2-bisfluoromethyl-3,4-dihydro-4-(2-pyridyloxy)-2H-1-benzopyran-3-ol (Compound 7-1), Trans-6-pentafluoroethyl-2,2-bisfluoromethyl-3,4-dihydro-4-(1,2-dihydro-2-oxo-1-pyridyl)-2H-1-benzopyran-3-ol (Compound 7-2)

A mixture of 0.42 g of 3,4-epoxy-6-pentafluoroethyl-2,2-bisfluoromethyl-3,4-dihydro-2H-1-benzopyran, 0.21 g of 2-hydroxypyridine, 0.11 g of pyridine and 4 ml of ethanol was refluxed for 3 hours and the solvent was distilled off. The resultant residue was purified using silica gel column chromatography (developing solution, MeOH:CH$_2$Cl$_2$=1:99) to obtain from the first eluted fraction 0.11 g of oily trans-6-pentafluoroethyl-2,2-bisfluoromethyl-3,4-dihydro-4-(2-pyridyloxy)-2H-1-benzopyran-3-ol represented by the following formula.

NMR(CDCl$_3$)δ: 4.20–4.60(1H,m), 4.73(4H,brd), 5.00–5.37(1H,m), 5.89(1H,d), 6.80–7.13(3H,m), 7.27–7.88(3H,m), 8.07(1H,dd).
MS m/z: 425(M$^+$)

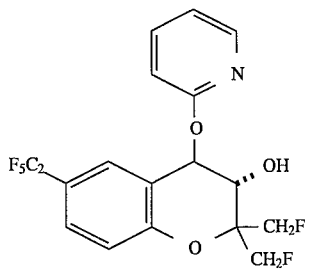

From the following eluted fraction, 0.29 g of trans-6-pentafluoroethyl-2,2-bisfluoromethyl-3,4-dihydro-4-(1,2-dihydro-2-oxo-1-pyridyl)-2H-1-benzopyran-3-ol represented by the following formula having a melting point of 162°–164° C. was obtained.

NMR (CDCl$_3$)δ: 4.12–4.55(1H,m), 4.73(2H,d), 4.78(2H, d), 4.95–5.60(1H,m), 6.05–6.70(3H,m), 6.70–7.04(2H, m), 7.10–7.55 (3H, m).

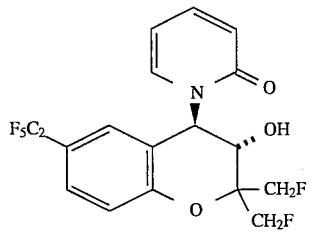

EXAMPLE 8

6-Pentafluoroethyl-2,2-bisfluoromethyl-4-(1,2-dihydro-2-oxo-1-pyridyl)-2H-1-benzopyran (Compound 8)

A mixture of 0.15 g of trans-6-pentafluoroethyl-2,2-bisfluoromethyl-3,4-dihydro-4-(1,2-dihydro-2-oxo-1-pyridyl)-2H-1-benzopyran-3-ol, 0.07 g of methanesulfonyl chloride, 0.08 g of triethylamine and 10 ml of tetrahydrofuran was stirred at room temperature for 8 hours and the solvent was distilled off. Water was added thereto and the mixture was extracted with methylene chloride. After the organic layer was washed with water and dried, the solvent was distilled off. The resultant residue was dissolved in 4 ml of tetrahydrofuran and 0.06 g of sodium hydrate (60%) was added thereto with stirring under ice-cooling. The mixture was then stirred at room temperature for 66 hours. Ice water was added thereto and the mixture was extracted with methylene chloride. After the organic layer was washed with water and dried, the solvent was distilled off. The resultant residue was purified using silica gel column chromatography (developing solution, MeOH:CH$_2$Cl$_2$=1:99) to obtain 0.09 g of 6-pentafluoroethyl-2,2-bisfluoromethyl-4-(1,2-dihydro-2-oxo-1-pyridyl)-2H-1-benzopyran represented by the following formula having a melting point of 137°–138° C.

NMR(CDCl$_3$)δ: 4.69(4H,d), 5.84(1H,s), 6.26(1H,td), 6.65(1H,brd), 6.82–7.05(1H,m), 7.13(1H,brs), 7.19–7.74(3H,m).
MS m/z: 407(M$^+$)

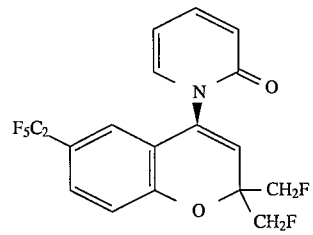

EXAMPLE 9

Trans-6-cyano-2,2-bisfluoromethyl-3,4-dihydro-4-(1,2-dihydro-2-oxo-1-pyridyl)-2H-1-benzopyran-3-ol (Compound 9)

Trans-6-cyano-2,2-bisfluoromethyl-3,4-dihydro-4-(1,2-dihydro-2-oxo-1-pyridyl)-2H-1-benzopyran-3-ol represented by the following formula having a melting point of 213°–214° C. was obtained according to the same method as in Example 7.

200 MHz-NMR(CDCl$_3$)δ: 4.21–4.40(1H,m), 4.53–4.93(4H,m), 5.03(1H,d), 6.29(1H,dd), 6.46(1H,d), 6.61(1H,d), 6.96(1H,d), 7.09(1H,d), 8.39(1H,dd), 8.54(1H, d).

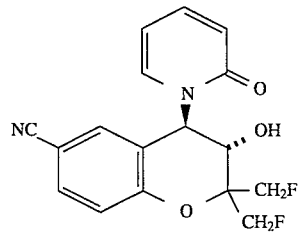

EXAMPLE 10

6-Cyano-2,2-bisfluoromethyl-4-(1,2-dihydro-2-oxo-1-pyridyl)-2H-1-benzopyran (Compound 10)

A mixture of 0.13 g of trans-6-cyano-2,2-bisfluoromethyl-3,4-dihydro-4-(1,2-dihydro-2-oxo-1-pyridyl)-2H-1-benzopyran-3-ol, 0.13 g of sodium hydroxide on support and 2 ml of dioxane was refluxed for 45 minutes. Water was added thereto and the mixture was extracted with ethyl acetate. After the organic layer was washed with water and dried, the solvent was distilled off. The resultant residue was recrystallized from ethyl acetate to obtain 6-cyano-2,2-bisfluoromethyl-4-(1,2-dihydro-2-oxo-1-pyridyl)- 2H-1-benzopyran represented by the following formula having a melting point of 174°–175° C.

200 MHz-NMR(CDCl$_3$)δ: 4.44–4.89(4H,m), 5.85(1H,s), 6.29 (1H, dt), 6.66 (1H,d), 6.98–7.07(2H, m), 7.14(1H,dd), 7.42–7.56(2H,m).

MS m/z: 314(M$^+$)

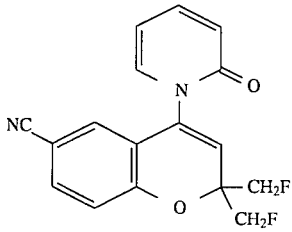

EXAMPLE 11

Trans-2,2-bisfluoromethyl-3,4-dihydro-6-nitro-4- (1,2-dihydro-2-oxo-1-pyridyl)-2H-1-benzopyran-3-ol (Compound 11)

Trans-2,2-bisfluoromethyl-3,4-dihydro-6-nitro-4-(1,2-dihydro-2-oxo-1-pyridyl)-2H-1-benzopyran-3-ol represented by the following formula having a melting point of 226°–228° C. was obtained according to the same method as in Example 7.

NMR(CDCl$_3$-DMSO-d$_6$)δ: 3.20–3.80(1H,m), 4.10–5.50(1H,m), 4.73(4H,d), 6.10–6.80(3H,m), 7.12(1H, d), 7.30–7.90(3H,m), 8.05(1H,dd).

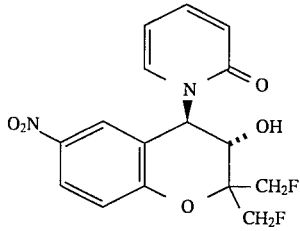

EXAMPLE 12

2,2-Bisfluoromethyl-6-nitro-4-(1,2-dihydro-2-oxo-1-pyridyl)-2H-1-benzopyran (Compound 12)

2,2-Bisfluoromethyl-6-nitro-4-(1,2-dihydro-2-oxo-1-pyridyl)-2H-1-benzopyran represented by the following formula having a melting point of 171°–173° C. was obtained according to the same method as in Example 10.

NMR(CDCl$_3$)δ: 4.68(4H,d), 5.69(1H,s), 6.30(1H,td), 6.63(1H,d), 7.02(1H,d), 7.08–7.70(3H,m), 8.10(1H, dd).

MS m/z : 334(M$^+$)

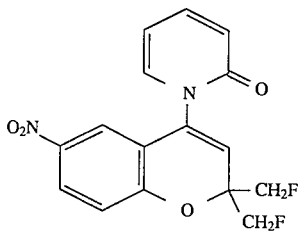

EXAMPLE 13

2,2-Bisfluoromethyl-6-nitro-4-(1,2-dihydro-2-thioxo-1-pyridyl)-2H-1-benzopyran (Compound 13)

A mixture of 0.13 g of 2,2-bisfluoromethyl-6-nitro-4-(1, 2-dihydro-2-oxo-1-pyridyl)-2H-1-benzopyran, 83 mg of a Lawesson's reagent, 1 ml of benzene and 1 ml of 1,2-dichloroethane was refluxed for 3 hours and the solvent was distilled off. The resultant residue was purified using silica gel column chromatography (developing solution, CH$_2$Cl$_2$), and then, recrystallized from a mixture of ethyl acetate and hexane to obtain 0.05 g of 2,2-bisfluoromethyl-6-nitro-4-(1, 2-dihydro-2-thioxo-1-pyridyl)-2H-1-benzopyran represented by the following formula having a melting point of 209°–210° C.

NMR(CDCl$_3$)δ: 4.76(4H,d), 5.90(1H, s), 6.75(1H,td), 7.07(1H,d), 7.20–7.90(4H,m), 8.16(1H,dd).

MS m/z: 350(M$^+$)

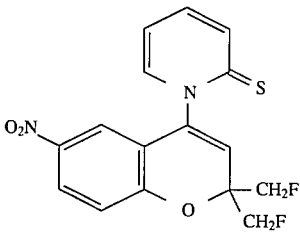

EXAMPLE 14

4-(2-Cyanoimino-1,2-dihydro-1-pyridyl)-2,2-bisfluoromethyl-6-nitro-2H-1-benzopyran (Compound 14)

A mixture of 0.09 g of 2,2-bisfluoromethyl-6-nitro-4-(1, 2-dihydro-2-thioxo-1-pyridyl)-2H-1-benzopyran, 0.20 g of methyl iodide and 5 ml of tetrahydrofuran was refluxed for 50 minutes. To the mixture were added 57 mg of cyanamide and 13 mg of sodium hydride (60%) and the mixture was refluxed for 1.5 hours. Methylene chloride was added thereto and the mixture was filtered to remove insoluble materials. The mother liquor was distilled off and the resultant residue was purified using silica gel column chromatography (developing solution, AcOEt:hexane=1:1) to obtain 0.05 g of 4-(2-cyanoimino-1,2-dihydro-1-pyridyl)-2, 2-bisfluoromethyl-6-nitro-2H-1-benzopyran represented by the following formula having a melting point of 238°–240° C.

NMR(CDCl$_3$-DMSO-d$_6$)δ: 4.70(4H,d), 6.26(1H, s), 6.82(1H,td), 7.16(1H,d), 7.25–7.50(2H,m), 7.70–8.00(2H, m), 8.18(1H, dd).

MS m/z: 358(M$^+$)

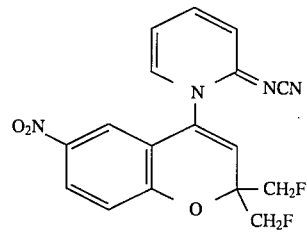

EXAMPLE 15

Trans-3-acetoxy-4-(N-acetyl-N-benzyloxy)amino-6-pentafluoroethyl-2,2-bisfluoromethyl-3,4,-dihydro-2H-1-benzopyran (Compound 15-1), Trans-4-(N-acetyl-N-benzyloxyl)amino-6-pentafluoroethyl-2,2-bisfluoromethyl-3,4-dihydro-2H-1-benzopyran-3-ol (Compound 15-2)

A mixture of 0.45 g of 3,4-epoxy-6-pentafluoroethyl-2,2-bisfluoromethyl-3,4-dihydro-2H-1-benzopyran, 0.25 g of benzyloxyamine hydrochloride, 0.28 g of triethylamine and 4 ml of ethanol was refluxed for 10 hours. After the solvent was distilled off, water was added thereto and the mixture was extracted with a mixed solvent of ethyl acetate and ether. The organic layer was washed with a saturated saline solution and dried. The solvent was distilled off and the resultant residue was purified using silica gel column chromatography (developing solution, MeOH:CH$_2$Cl$_2$=1:99) to obtain 0.43 g of trans-4-(N-benzyloxy)amino-6-pentafluoroethyl-2,2-bisfluoromethyl-3,4-dihydro-2H-1-benzopyran-3-ol. This compound was dissolved in a mixture of 0.40 ml of pyridine and 4 ml of chloroform and to the solution was added 0.10 ml of acetyl chloride with stirring under ice-cooling. The mixture was stirred under ice-cooling for 30 minutes and then stirred at room temperature for 1 hour. Diluted hydrochloric acid was added thereto and the mixture was extracted with methylene chloride. After the organic layer was washed with water and dried, the solvent was distilled off. The resultant residue was purified using silica gel column chromatography (developing solution, MeOH:CH$_2$Cl$_2$=1:99) to obtain from the first eluted fraction 0.15 g of trans-3-acetoxy-4-(N-acetyl-N-benzyloxy)amino-6-pentafluoroethyl-2,2-bisfluoromethyl-3,4-dihydro-2H-1-benzopyran represented by the following formula having a melting point of 107°–108° C.

NMR(CDCl$_3$)δ: 2.05(3H,s), 2.20(3H,s), 4.48(1H,d), 4.57(2H,dd), 4.70(2H,dd), 4.75(1H,d), 5.76(1H,d), 5.91–6.20(1H,m), 6.89–7.29(6H,m), 7.42(1H,dd), 7.51(1H, brs).

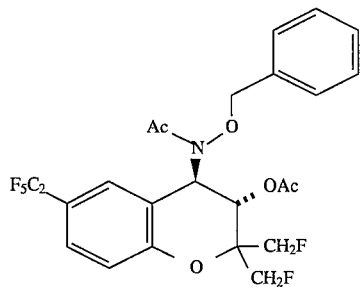

From the following eluted fraction, 0.20 g of trans-4-(N-acetyl-N-benzyloxy)amino-6-pentafluoroethyl-2,2-bisfluoromethyl-3,4-dihydro-2H-1-benzopyran-3-ol represented by the following formula having a melting point of 98°–1000° C. was obtained.

NMR(CDCl$_3$)δ: 2.23 (3H, s), 4.45–4.97(4H, m), 4.70(4H, d), 5.35–6.04(1H,m), 6.91–7.43(7H,m), 7.50(1H,brs).

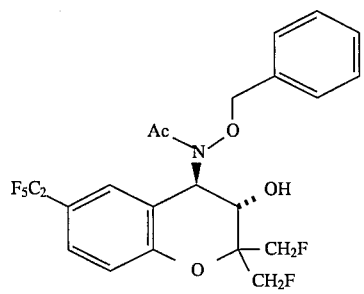

EXAMPLE 16

Trans-4-(N-acetyl-N-hydroxy)amino-6-pentafluoroethyl-2,2-bisfluoromethyl-3,4-dihydro-2H-1-benzopyran-3-ol (Compound 16)

A mixture of 0.10 g of trans-4-(N-acetyl-N-benzyloxy)amino-6-pentafluoroethyl-2,2-bisfluoromethyl-3,4-dihydro-2H-1-benzopyran-3-ol, 90 mg of 10% palladium carbon and 8 ml of ethanol was subjected to catalytic reduction under hydrogen stream at room temperature. Insoluble materials were removed by vacuum filtration and the mother liquor was distilled off. The resultant residue was purified using silica gel column chromatography (developing solution, MeOH:CH$_2$Cl$_2$=1:99) to obtain 0.06 g of trans-4-(N-acetyl-N-hydroxy)amino-6-pentafluoroethyl-2,2-bisfluoromethyl-3,4-dihydro-2H-1-benzopyran-3-ol represented by the following formula having a melting point of 67°–70° C.

NMR(CDCl$_3$)δ: 2.30(3H,s), 4.40–4.76(2H,m), 4.66(2H, brd), 4.70(2H,brd), 5.78(1H,brd), 7.01(1H,d), 7.25(1H,brs), 7.42(1H,brd), 8.70(1H,brs).

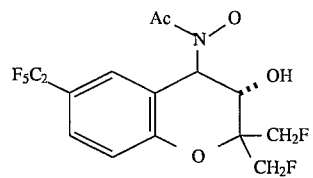

EXAMPLE 17

Trans-4-(N-acetyl-N-benzyloxy)amino-6-cyano-2,2-bisfluoromethyl-3,4-dihydro-2H-1-benzopyran-3-ol (Compound 17)

Trans-4-(N-acetyl-N-benzyloxy)amino-6-cyano-2,2-bisfluoromethyl-3,4-dihydro-2H-1-benzopyran-3-ol represented by the following formula having a melting point of 210°–212° C. was obtained according to the same method as in Example 15.

200 MHz-NMR(DMSO-d$_6$)δ: 2.26(3H,s), 4.67–5.08(7H, m), 6.48(1H,d), 7.08(1H,d), 7.33(5H,brs), 7.55(1H,d), 7.64(1H,dd).

MS m/z: 402(M$^+$)

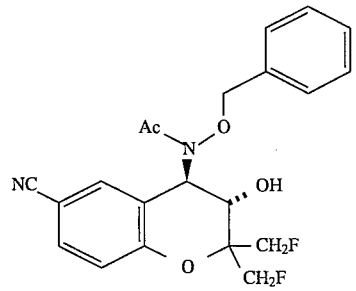

EXAMPLE 18

Trans-4-(N-acetyl-N-hydroxy)amino-6-cyano-2,2-bisfluoromethyl-3,4-dihydro-2H-1-benzopyran-3-ol (Compound 18)

Trans-4-(N-acetyl-N-hydroxy)amino-6-cyano-2,2-bisfluoromethyl-3,4-dihydro-2H-1-benzopyran-3-ol represented by the following formula having a melting point of 230°–232° C. was obtained according to the same method as in Example 16.

200 MHz-NMR(DMSO-d$_6$)δ: 2.17(3H, s), 4.24–4.37(1H, m), 4.46–5.07(5H,m), 5.60(1H,d), 6.14(1H,d), 7.05(1H,d), 7.37(1H,s), 7.64(1H,dd).

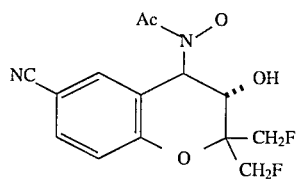

EXAMPLE 19

Trans-4-(N-acetyl-N-benzyloxy)amino-2,2-bisfluoromethyl-3,4-dihydro-6-nitro-2H-1-benzopyran-3-ol (Compound 19)

Trans-4-(N-acetyl-N-benzyloxy)amino-2,2-bisfluoromethyl-3,4-dihydro-6-nitro-2H-1-benzopyran-3-ol represented by the following formula having a melting point of 207°–210° C. was obtained according to the same method as in Example 15.

NMR(CDCl$_3$-DMSO-d$_6$)δ: 2.28(3H,s), 4.10–5.70(8H,m), 6.55(1H,d), 7.00–7.50(6H,m), 7.90–8.30(2H,m).

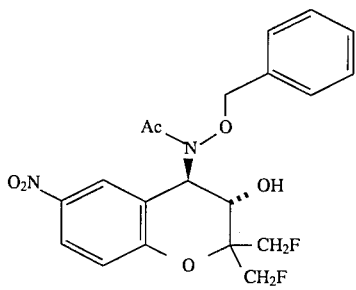

EXAMPLE 20

Trans-6-pentafluoroethyl-2,2-bisfluoromethyl-3,4-dihydro-4-(3-oxo-cyclopent-1-enyloxy)-2H-1-benzopyran-3-ol (Compound 20)

In 40 ml of tetrahydrofuran was dissolved 0.36 g of cyclopentan-1,3-dione and 0.13 g of sodium hydride (60%) was added thereto under nitrogen stream with cooling at −20° C. after the mixture was stirred at room temperature for 15 minutes, 0.72 g of a complex of copper (I) bromide and dimethyl sulfide was added. To the reaction mixture was added 0.92 g of 3,4-epoxy-6-pentafluoroethyl-2,2-bisfluoromethyl-3,4-dihydro-2H-1-benzopyran dissolved in 10 ml of tetrahydrofuran. The mixture was stirred for 6 days. To the mixture were added water and a small amount of concentrated sulfuric acid. The mixture was extracted with methylene chloride and the organic layer was washed with water and dried. The solvent was distilled off and the resultant residue was purified using silica gel column chromatography (developing solution, MeOH:CH$_2$Cl$_2$=1:99) and another silica gel column chromatography (developing solution, AcOEt:hexane=1:1) to obtain 0.04 g of trans-6-pentafluoroethyl-2,2-bisfluoromethyl-3,4-dihydro-4-(3-oxo-cyclopent-1-enyloxy)-2H-1-benzopyran-3-ol represented by the following formula having a melting point of 165°–167° C.

NMR(CDCl$_3$)δ: 2.34–2.87(4H,m), 4.12–4.38(2H,m), 4.82(4H,brd), 4.91–5.12(1H,m), 5.94(1H,s), 7.04(1H,d), 7.41(1H,brs), 7.50(1H,dd).

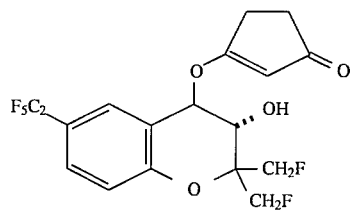

EXAMPLE 21

Trans-6-cyano-2,2-bisfluoromethyl-3,4-dihydro-4-(3-oxo-cyclopent-1-enyloxy)-2H-1-benzopyran-3-ol (Compound 21)

Trans-6-cyano-2,2-bisfluoromethyl-3,4-dihydro-4-(3-oxo-cyclopent-1-enyloxy)-2H-1-benzopyran-3-ol represented by the following formula having a melting point of 200°–201° C. was obtained according to the same method as in Example 20.

NMR(CDCl$_3$)δ: 2.38–2.93(4H,m), 4.22–5.58(6H,m), 5.87(1H,s), 7.08(1H,d), 7.50–7.83(2H,m).

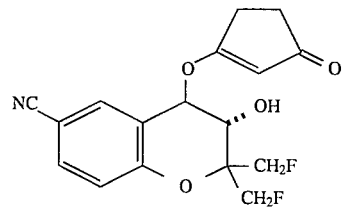

EXAMPLE 22

Trans-2,2-bisfluoromethyl-3,4-dihydro-6-nitro-4-(3-oxo-cyclopent-1-enyloxy)-2H-1-benzopyran-3-ol (Compound 22)

Trans-2,2-bisfluoromethyl-3,4-dihydro-6-nitro-4-(3-oxo-cyclopent-1-enyloxy)-2H-1-benzopyran-3-ol represented by the following formula having a melting point of 206°–208° C. was obtained according to the same method as in Example 20.

NMR(CDCl$_3$-DMSO-d$_6$)δ: 2.20–2.90(4H,m), 4.10–4.60(1H,m), 4.69(2H,d), 4.80(2H,d), 5.38(1H,d), 5.78(1H,s), 6.47(1H,d), 7.13(1H,d), 8.00–8.30(2H,m).

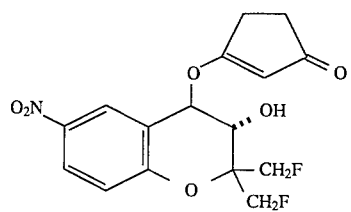

EXAMPLE 23

Trans-6-pentafluoroethyl-2,2-bisfluoromethyl-3,4-dihydro-4-[(1,6-dihydro-1-methyl-6-oxo-3-pyridazinyl)oxy]-2H-1-benzopyran-3-ol (Compound 23)

A mixture of 0.58 g of 3,4-epoxy-6-pentafluoroethyl-2,2-bisfluoromethyl-3,4-dihydro-2H-1-benzopyran, 0.22 g of 3-hydroxy-1-methyl-1,6-dihydropyridazin-6-one, 0.16 g of pyridine and 5 ml of ethanol was refluxed for 5 hours. The solvent was distilled off and the resultant residue was purified using silica gel column chromatography (developing solution, MeOH:CH$_2$Cl$_2$=1:99) to obtain 0.60 g of trans-6-pentafluoroethyl-2,2-bisfluoromethyl-3,4-dihydro- 4-[(1,6-dihydro-1-methyl-6-oxo-3-pyridazinyl)oxy]-2H-1-benzopyran-3-ol represented by the following formula having a melting point of 189°–191° C. in Example 20.

NMR(CDCl$_3$)δ: 3.64(3H,s), 4.23–4.60(1H,m), 4.73(2H, d), 4.81(2H,d), 5.00–5.37(1H,m), 6.00(1H,d), 6.81(1H,d), 7.00(1H,d), 7.04(1H,d), 7.47(1H,dd), 7.53(1H,s).

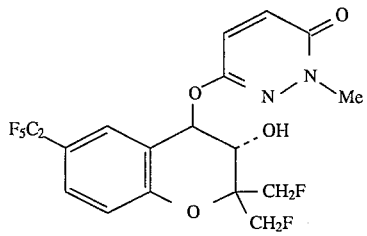

EXAMPLE 24

Trans-6-cyano-2,2-bisfluoromethyl-3,4-dihydro-4-[(1,6-dihydro-1-methyl-6-oxo-3-pyridazinyl)oxy]-2H-1-benzopyran-3-ol (Compound 24)

Trans-6-cyano-2,2-bisfluoromethyl-3,4-dihydro-4-[(1,6-dihydro-1-methyl-6-oxo-3-pyridazinyl)oxy]-2H-1-benzopyran-3-ol represented by the following formula having a melting point of 215°–217° C. was obtained according to the same method as in Example 23.

200 MHz-NMR(DMSO-d$_6$)δ: 3.61(3H,s), 4.27(1H,dd), 4.47–5.01(4H,m), 5.87(1H,d), 6.46(1H,d), 7.00(1H,d), 7.11(1H,d), 7.23(1H,d), 7.72(1H,dd), 7.84(1H,d).

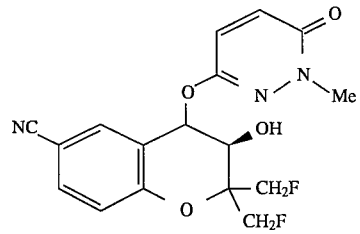

EXAMPLE 25

Trans-2,2-bisfluoromethyl-3,4-dihydro-4-[(1,6-dihydro-1-methyl-6-oxo-3-pyridazinyl)oxy]-6-nitro-2H-1-benzopyran-3-ol (Compound 25)

Trans-2,2-bisfluoromethyl-3,4-dihydro-4-[(1,6-dihydro-1-methyl-6-oxo-3-pyridazinyl)oxy]-6-nitro-2H-1-benzopyran-3-ol represented by the following formula having a melting point of 226°–228° C. was obtained according to the same method as in Example 23.

NMR(CDCl$_3$-DMSO-d$_6$)δ: 3.60(3H,s), 4.10–4.50(1H,m), 4.70(4H,d), 5.86(1H,d), 6.34(1H,d), 6.88(1H,d), 7.04(1H,d), 7.13(1H,d), 7.90–8.40(2H,m).

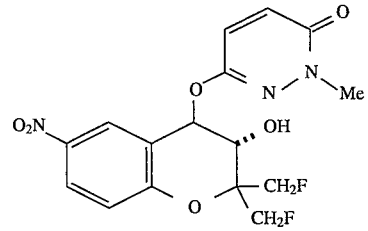

EXAMPLE 26

6-Pentafluoroethyl-2,2-bisfluoromethyl-4-[(1,6-dihydro-1-methyl-6-oxo-3-pyridazinyl)oxy]-2H-1-benzopyran (Compound 26)

6-Pentafluoroethyl-2,2-bisfluoromethyl-4-[(1,6-dihydro-1-methyl-6-oxo-3-pyridazinyl)oxy]-2H-1-benzopyran represented by the following formula having a melting point of 150°–152° C. was obtained according to the same method as in Example 8.

NMR(CDCl$_3$)δ: 3.65(3H,s), 4.58(4H,brd), 5.80(1H,s), 7.01(1H,d), 7.02(1H,d), 7.18(1H,d), 7.50 (1H, dd), 7.57 (1H, brs).

MS m/z: 438(M$^+$)

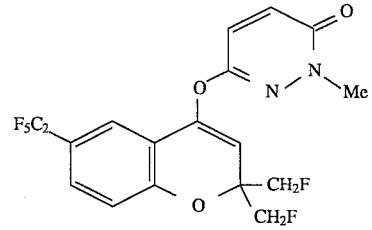

EXAMPLE 27

Trans-2,2-bisfluoromethyl-3,4-dihydro-4-(2,3-dihydro-1-oxo-1H-isoindol-2-yl)-6-nitro-2H-1-benzopyran-3-ol (Compound 27)

(1) A mixture of 0.53 g of 3,4-epoxy-2,2-bisfluoromethyl-3,4-dihydro-6-nitro-2H-1-benzopyran, 15 ml of a concentrated aqueous ammonia solution and 15 ml of ethanol was stirred at room temperature for 42 hours. The solvent was distilled off and methylene chloride was added thereto. The mixture was extracted with 1N hydrochloric acid and 2N sodium hydroxide was added to an aqueous layer to form an alkaline solution. The solution was extracted with methylene chloride and the organic layer was washed with water and dried. The solvent was distilled off and the resultant residue was recrystallized from a mixed solvent of ethyl acetate and hexane to obtain 0.32 g of 4-amino-2,2-bisfluoromethyl-3,4-dihydro-6-nitro-2H-1-benzopyran-3-ol represented by the following formula having a melting point of 174°–177° C. (decomp.).

NMR(CDCl$_3$-DMSO-d$_6$)δ: 2.80(3H,brs), 3.50–4.00(2H, m), 4.72(4H,d), 6.93(1H,d), 7.98(1H,dd), 8.50(1H,d).

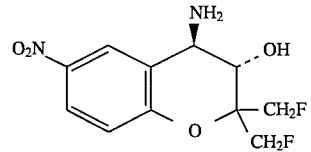

(2) A mixture of 0.25 g of 4-amino-2,2-bisfluoromethyl-3,4-dihydro-6-nitro-2H-1-benzopyran-3-ol, 0.22 g of methyl 2-bromomethylbenzoate, 0.40 g of potassium carbonate, 0.09 g of potassium iodide and 5 ml of acetonitrile was stirred at 75°–85° C. for 6 hours. Water was added thereto and the mixture was extracted with a mixed solvent of ethyl acetate and ether. After the organic layer was washed with 1N hydrochloric acid and dried, the solvent was distilled off. The resultant residue was purified using silica gel column chromatography (developing solution, AcOEt: hexane=1:1) and recrystallized from a mixed solvent of ethyl acetate and hexane to obtain 0.15 g of trans-2,2-bisfluoro-methyl-3,4-dihydro-4-(2,3-dihydro-1-oxo-1H-isoindol-2-yl)-6-nitro-2H-1-benzopyran-3-ol represented by the following formula having a melting point of 285°–288° C.

200 MHz-NMR(CDCl$_3$-DMSO-d$_6$)δ: 4.16–5.20(7H,m), 5.50(1H,d), 6.46(1H,d), 7.18(1H,d), 7.50–7.75(4H,m), 7.82(1H,d), 8.08(1H,dd).

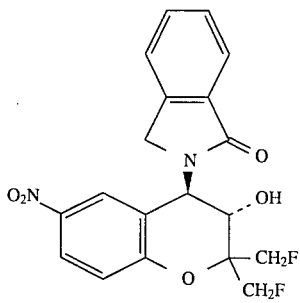

EXAMPLE 28

2-(6-Cyano-2,2-bisfluoromethyl-2H-1-benzopyran-4-yl)pyridine N-oxide (Compound 28)

(1) To a mixture of 0.20 g of 6-cyano-2,2-bisfluoromethyl-3,4-dihydro-2H-1-benzopyran-4-one, 3.09 g of dimethylaminopyridine and 12 ml of dry methylene chloride was added dropwise 0.35 ml of trifluoromethanesulfonic anhydride with stirring under ice-cooling. The mixture was stirred under ice-cooling for 15 minutes and then stirred at room temperature for 1 hour. .Water was added thereto and the mixture was extracted with methylene chloride. After the organic layer was washed with water and dried, the solvent was distilled off. The resultant residue was purified using silica gel column chromatography (developing solution, CH$_2$Cl$_2$:hexane=1:1) to obtain 0.12 g of oily 6-cyano-4-trifluoromethanesulfonyloxy-2,2-bisfluoromethyl-2H-1-benzopyran represented by the following formula.

NMR(CDCl$_3$)δ: 4.59(4H,d), 5.80(1H,s), 6.99(1H,d), 7.72–7.39(2H,m).

MS m/z: 369(M$^+$)

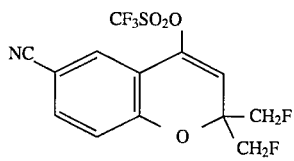

(2) A mixture of 120 mg of 6-cyano-4-trifluoromethanesulfonyloxy-2,2-bisfluoromethyl-2H-1-benzopyran, 87 mg of 2-trimethylstannylpyridine, 25.4 mg of tris-dibenzylidene acetone chloroform dipalladium (0), 12.8 mg of triphenylphosphine, 110 mg of lithium chloride and 6 ml of dry tetrahydrofuran was refluxed for 6.5 hours. After cooling, ether was added and the mixture was filtered using Celite. After the organic layer of the mother liquor was washed with water and dried, the solvent was distilled off. The resultant residue was purified using silica gel column chromatography (developing solution, CH$_2$Cl$_2$) to obtain 80 mg of oily 6-cyano-2,2-bisfluoromethyl-4-(2-pyridyl)-2H-1-benzopyran represented by the following formula.

NMR(CDCl$_3$)δ: 4.58(4H,d), 5.93(1H,s), 6.97(1H,d), 7.18–7.99(5H,m), 8.53–8.83(1H,m).

MS m/z: 298(M$^+$)

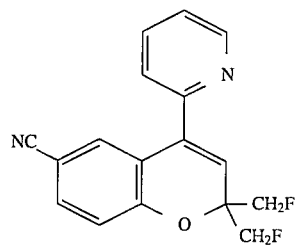

(3) In 3 ml of methylene chloride was dissolved 80 mg of 6-cyano-2,2-bisfluoromethyl-4-(2-pyridyl)-2H-1-benzopyran and 75.7 mg of m-chloroperbenzoic acid (70%) was added thereto with stirring under ice-cooling. The mixture was stirred at room temperature for 15 hours. After addition of 28 mg of m-chloroperbenzoic acid (70%), the mixture was further stirred for 19 hours. Sodium bicarbonate solution was added thereto and the mixture was extracted with methylene chloride. After the organic layer was washed with water and dried, the solvent was distilled off. The resultant residue was purified using silica gel column chromatography (developing solution, MeOH:CH$_2$Cl$_2$=1:99) to obtain 30 mg of 2-(6-cyano-2,2-bisfluoromethyl-2H-1-benzopyran-4-yl)pyridine N-oxide represented by the following formula having a melting point of 204°–207° C.

NMR(CDCl$_3$)δ: 4.63(4H,d), 5.89(1H,s), 6.82–7.62(6H, m), 8.13–8.47(1H,m).

MS m/z: 314(M$^+$)

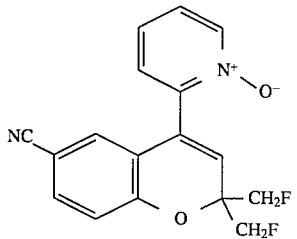

EXAMPLE 29

2-(2,2-Bisfluoromethyl-6-nitro-2H-1-benzopyran-4-yl)pyridine N-oxide (Compound 29)

(1) Using 2,2-bisfluoromethyl-3,4-dihydro-6-nitro-2H-1-benzopyran-4-one as a starting material, oily 4-trifluoromethanesulfonyloxy-2,2-bisfluoromethyl-6-nitro-2H-1-benzopyran represented by the following formula was obtained according to the same method as in Example 28.

NMR(CDCl$_3$)δ: 4.54(4H,d), 5.74(1H,s), 6.93(1H,d), 7.88–8.21(2H,m).

MS m/z: 389(M$^+$)

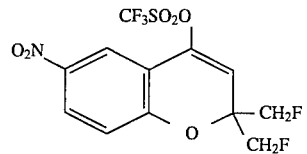

(2) Oily 2,2-bisfluoromethyl-6-nitro-4-(2-pyridyl)-2H-1-benzopyran represented by the following formula was obtained according to the same method as in Example 28.

NMR(CDCl$_3$)δ: 4.62(4H,d), 5.98(1H,s), 7.00(1H,d), 7.18–7.57(2H,m), 7.75(1H,dd), 8.07(1H,dd), 8.27(1H,d), 8.60–8.83(1H,m).

MS m/z: 318(M⁺)

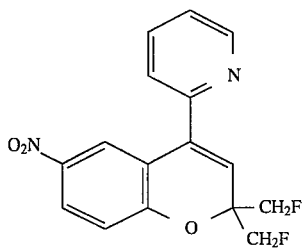

(3) 2-(2,2-Bisfluoromethyl-6-nitro-2H-1-benzopyran-4-yl)pyridine N-oxide represented by the following formula having a melting point of 183°–184° C. was obtained according to the same method as in Example 28.

NMR(CDCl₃)δ: 4.65(4H,d), 5.95(1H,s), 7.00(1H,d), 7.35–7.88(4H,m), 8.07(1H,dd), 8.20–8.50(1H,m).

MS m/z: 334(M⁺)

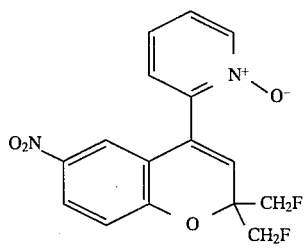

EXAMPLE 30

2,2-Bisfluoromethyl-6-nitro-4-(2-oxo-1-pyrrolidinyl)-2H-1,3-benzoxazine (Compound 30)

(1) A mixture of 0.09 g of 2,2-bisfluoromethyl-3,4-dihydro-6-nitro-2H-1,3-benzoxazin-4-one, 0.18 g of phosphorus pentachloride and 1 ml of phosphorus oxychloride was stirred at room temperature for 20 minutes and the mixture was stirred at 40°–60° C. for 3 hours. The solvent was distilled off and the resultant residue was purified using silica gel column chromatography (developing solution, CH₂Cl₂) to obtain 0.10 g of 4-chloro-2,2-bisfluoromethyl-6-nitro-2H-1,3-benzoxazine represented by the following formula having a melting point of 75°–77° C.

NMR(CDCl₃)δ: 4.66(4H,d), 7.07(1H,d), 8.38(1H,dd), 8.55(1H,d).

MS m/z: 275(M⁺)

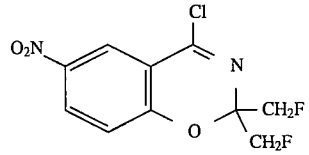

(2) In 1 ml of N,N-dimethylformamide was dissolved 62 mg of 2-pyrrolidinone and 35 mg of sodium hydride (60%) was added thereto under nitrogen stream. The mixture was stirred at room temperature for 20 minutes and 90 mg of 4-chloro-2,2-bisfluoromethyl-6-nitro-2H-1,3-benzoxazine dissolved in 2 ml of N,N-dimethylformamide was added thereto. The mixture was stirred at 45°–55° C. for 5 hours. After addition of saturated saline solution, the mixture was extracted with ethyl acetate. The organic layer was washed with saturated saline solution and dried. The solvent was distilled off and the resultant residue was purified using silica gel column chromatography (developing solution, MeOH:CH₂Cl₂=1:99) to obtain 50 mg of 2,2-bisfluoromethyl-6-nitro-4-(2-oxo-1-pyrrolidinyl)-2H-1,3-benzoxazine represented by the following formula having a melting point of 195°–198° C.

NMR(CDCl₃)δ: 1.80–2.70(4H,m), 3.62(2H,t), 4.66(2H, dd), 4.85(2H,d), 7.12(1H,d), 8.33(1H,dd), 8.65(1H,d).

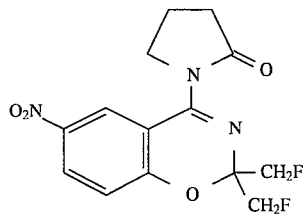

EXAMPLE 31

Trans-6-cyano-2,2-bisfluoromethyl-4-(1,2-dihydro-2-oxo-4-pyridyloxy)-2H-1-benzopyran-3-ol (Compound 31)

A mixture of 250 mg of 6-cyano-3,4-epoxy-2,2-bisfluoromethyl-3,4-dihydro-2H-1-benzopyran, 116 mg of 2,4-dihydroxypyridine, 4 ml of ethyl alcohol and 0.084 ml of pyridine was refluxed with heating for 4 hours. The solvent was distilled off and the resultant residue was purified using silica gel column chromatography (developing solution, MeOH:CH₂Cl₂=1:99) to obtain 71 mg of trans-6-cyano-2, 2-bisfluoromethyl-4-(1,2-dihydro-2-oxo-4-pyridyloxy)-2H-1-benzopyran-3-ol represented by the following formula having a melting point of 249°–250° C.

270 MHz-NMR(DMSO-d₆)δ: 4.17(1H,brs), 4.49(1H,d), 4.66–4.97(4H,m), 5.38(1H,d), 5.96(1H,dd), 6.16(1H,d), 6.48(1H,brs), 7.13(1H,d), 7.31(1H,d), 7.76(1H,dd), 7.82(1H,s).

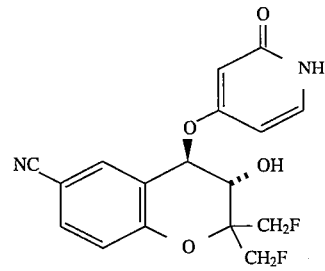

EXAMPLE 32

Trans-2,2-bisfluoromethyl-6-heptafluoropropyl-3,4-dihydro-4-(2-oxo-1-pyrrolidinyl)-2H-1-benzopyran-3-ol (Compound 32)

(1) A mixture of 4.4 g of 2,2-bisfluoromethyl-6-iode-2H-1-benzopyran, 34.3 g of potassium heptafluorobutyrate, 26.2 g of copper (I) iodide, 40 ml of toluene and 100 ml of N,N-dimethylformamide was stirred at 110° C. with heating for 1 hour. The mixture was stirred at 150° C. with heating for 3 hours while toluene was distilled off. To the reaction mixture was added a mixture of 2N hydrochloric acid and ethyl acetate and the resultant mixture was filtered using Celite to remove insoluble materials. The filtrate was extracted with ethyl acetate and the mixture was washed with 10% sodium sulfite and saturated saline solution. The mixture was dried with sodium sulfate and the solvent was distilled off. The resultant residue was purified using silica gel column chromatography (developing solution, hexane:CH₂Cl₂=5:1) to obtain 2.5 g of oily 2,2-bisfluoromethyl-6-heptafluoropropyl-2H-1-benzopyran represented by the following formula.

NMR(CDCl₃)δ: 4.49(4H,d), 5.60(1H,d), 6.55(1H,d), 6.83(1H,d), 7.11(1H,d), 7.28(1H,dd).

MS m/z: 364(M⁺)

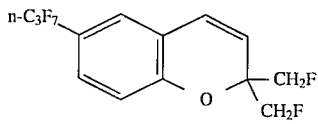

(2) A mixture of 3.1 g of 2,2-bisfluoromethyl-6-heptafluoropropyl-2H-1-benzopyran, 4.20 g of m-chloroperbenzoic acid (70%) and 50 ml of methylene chloride was stirred at room temperature for 27 hours. After removal of the separated crystal by filtration, the filtrate was washed with saturated sodium hydrogen carbonate solution and saturated saline solution, and dried with sodium sulfate. The solvent was distilled off and the resultant residue was purified using silica gel column chromatography (developing solution, hexane:CH₂Cl₂=5:1) to obtain 1.44 g of oily 3,4-epoxy-2,2-bisfluoromethyl-6-heptafluoropropyl-3,4-dihydro-2H-1-benzopyran represented by the following formula.

NMR(CDCl₃)δ: 3.85 (1H, d ), 4.06(1H,d), 4.69(4H,d), 7.00(1H, d ), 7.54(1H,dd), 7.61(1H,d).

MS m/z: 380(M⁺)

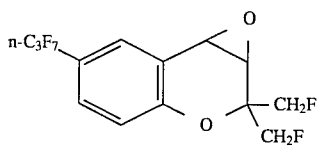

(3) Using 3,4-epoxy-2,2-bisfluoromethyl-6-heptafluoropropyl-3,4-dihydro-2H-1-benzopyran, trans-2,2-bisfluoromethyl-6-heptafluoropropyl-3,4-dihydro-4-(2-oxo-1-pyrrolidinyl)-2H-1-benzopyran-3-ol represented by the following formula having a melting point of 174°–175° C. was obtained according to the same method as in Example 1.

NMR(CDCl₃)δ: 1.90–2.75(4H,m), 2.75–3.70(2H,m), 4.05–4.50(1H,m), 4.73(4H,d), 4.80–5.30(1H,m), 5.43(1H, d ), 7.04(1H,d), 7.10(1H,d), 7.43(1H, dd).

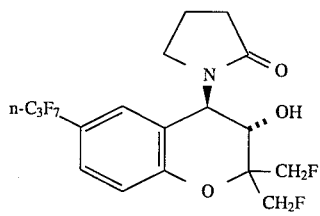

EXAMPLE 33

2,2-Bisfluoromethyl-6-heptafluoropropyl-4-(2-oxo-1-pyrrolidinyl)-2H-1-benzopyran (Compound 33)

Using trans-2,2-bisfluoromethyl-6-heptafluoropropyl-3,4-dihydro-4-(2-oxo-1-pyrrolidine)-1H-1-benzopyran-3-ol as a starting material, oily 2,2-bisfluoromethyl-6-heptafluoropropyl-4-(2-oxo-1-pyrrolidinyl)-2H-1-benzopyran represented by the following formula was obtained according to the same method as in Example 10.

NMR(CDCl₃)δ: 2.00–2.80(4H,m), 3.61(2H,t), 4.54(4H, d), 5.64(1H,s), 6.99(1H,d), 7.13(1H,d), 7.40(1H, dd).

MS m/z: 447(M⁺)

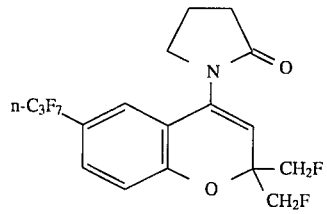

EXAMPLE 34

Trans-2,2-bisfluoromethyl-6-trifluoromethyl-3,4-dihydro-4-(2-oxo-1-pyrrolidinyl)-2H-1-benzopyran-3-ol (Compound 34)

(1 ) Using 2,2-bisfluoromethyl-6-iodo-2H-benzopyran and potassium trifluoroacetate, oily 2,2-bisfluoromethyl-6-trifluoromethyl-2H-1-benzopyran represented by the following formula was obtained according to the same method as in Example 32 (1).

NMR(CDCl₃)δ: 4.48(4H,d), 5.62(1H,d), 6.55(1H,d), 6.85 (1H,d), 7.22 (1H,d), 7.35(1H, dd).

MS m/z: 264(M⁺)

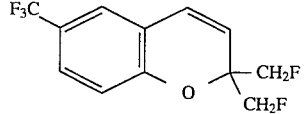

(2) Using 2,2-bisfluoromethyl-6-trifluoromethyl-2H-1-benzopyran, oily 3,4-epoxy-2,2-bisfluoromethyl-6-trifluoromethyl-3,4-dihydro-2H-1-benzopyran was obtained according to the same method as in Example 32 (2).

NMR(CDCl₃)δ: 3.78(1H,d), 4.00(1H,d), 4.65(4H,d), 6.90(1H, d ), 7.33–7.67(2H,m).

MS m/z: 280(M⁺)

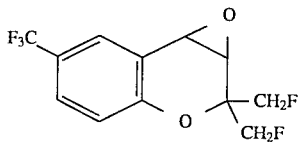

(3) Using 3,4-epoxy-2,2-bisfluoromethyl-6-trifluoromethyl-3,4-dihydro-2H-1-benzopyran, trans-2,2-bisfluoromethyl-6-trifluoromethyl-3,4-dihydro-4-(2-oxo-1-pyrrolidinyl)-2H-1-benzopyran-3-ol represented by the following formula having a melting point of 186°–187° C. was obtained according to the same method as in Example 1.

270 MHz-NMR(CDCl₃)δ: 2.12–2.14(2H,m), 2.56–2.64(2H,m), 3.06–3.25(1H,m), 3.28–3.36(2H,m), 4.23–4.29(1H,m), 4.63–4.91(4H,m), 5.47(1H,d), 7.07(1H, d), 7.19(1H,d), 7.48(1H,dd).

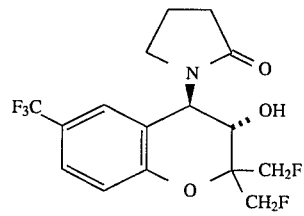

EXAMPLE 35

2,2-Bisfluoromethyl-6-trifluoromethyl-4-(2-oxo-1-pyrrolidinyl)-2H-1-benzopyran (Compound 35)

Using trans-2,2-bisfluoromethyl-6-trifluoromethyl-3,4-dihydro-4-(2-oxo-1-pyrrolidinyl)-2H-1-benzopyran-3-ol as a starting material, 2,2-bisfluoromethyl-6-trifluoromethyl-4-(2-oxo-1-pyrrolidinyl)-2H-1-benzopyran represented by the following formula having a melting point of 125°–127° C. was obtained according to the same method as in Example 10.

NMR (CDCl$_3$)δ: 2.01–2.78 (4H, m), 3.63(2H,t), 4.55(4H, d), 5.65(1H,s), 6.96(1H,d), 7.20(1H,d), 7.43 (1H, dd).

MS m/z: 347(M$^+$)

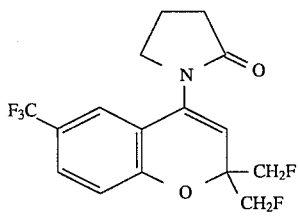

EXAMPLE 36

Trans-2,2-bisfluoromethyl-6-heptafluoropropyl-3,4-dihydro-4-(2-oxo-1-piperidinyl)-2H-1-benzopyran-3-ol (Compound 36)

Using 3,4-epoxy-2,2-bisfluoromethyl-6-heptafluoropropyl-3,4-dihydro-2H-1-benzopyran as a starting material, trans-2,2-bisfluoromethyl-6-heptafluoropropyl-3,4-dihydro-4-(2-oxo-1-piperidinyl)-2H-1-benzopyran-3-ol represented by the following formula having a melting point of 156°–157° C. was obtained according to the same method as in Example 4.

NMR(CDCl$_3$)δ: 1.50–2.20(4H,m), 2.35–3.55(4H,m), 4.05–4.65(1H,m), 4.74(4H,d), 4.86(1H,d), 6.05 (1H, dd ), 7.06(1H,d), 7.14(1H,d), 7.45(1H, dd).

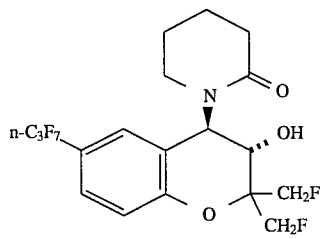

EXAMPLE 37

2,2-Bisfluoromethyl-6-heptafluoropropyl-4-(2-oxo-1-piperidinyl)-2H-1-benzopyran (Compound 37)

Using trans-2,2-bisfluoromethyl-6-heptafluoropropyl-3,4-dihydro-4-(2-oxo-1-piperidinyl)-2H-1-benzopyran-3-ol as a starting material, oily 2,2-bisfluoromethyl-6-heptafluoropropyl-4-(2-oxo-1-piperidinyl)-2H-1-benzopyran represented by the following formula was obtained according to the same method as in Example 10.

NMR(CDCl$_3$)δ: 1.60–2.20(4H,m), 2.30–2.80(2H,m), 3.20–3.70(2H,m), 4.59(4H,d), 5.65(1H,s), 6.97(1H,d), 7.04(1H,d), 7.38(1H,dd).

MS m/z: 461(M$^+$)

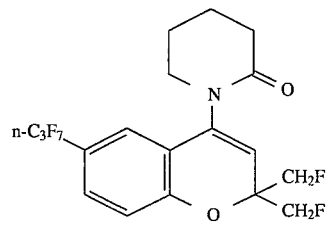

EXAMPLE 38

Trans-2,2-bisfluoromethyl-6-trifluoromethyl-3,4-dihydro-4-(2-oxo-1-piperidinyl)-2H-1-benzopyran-3-ol (Compound 38)

Using 3,4-epoxy-2,2-bisfluoromethyl-6-trifluoromethyl-3,4-dihydro-2H-1-benzopyran as a starting material, trans-2,2-bisfluoromethyl-6-trifluoromethyl-3,4-dihydro-4-(2-oxo-1-piperidinyl)-2H-1-benzopyran-3-ol represented by the following formula having a melting point of 184°–187° C. was obtained according to the same method as in Example 4.

NMR(CDCl$_3$)δ: 1.58–2.11(4H,m), 2.33–2.71(2H,m), 2.85–3.23(2H,m), 4.72(4H,d), 4.76–4.94(1H,m), 5.79–6.17(1H,m), 6.98(1H,d), 7.12(1H,d), 7.39(1H,dd).

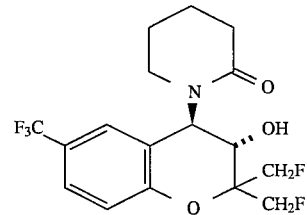

EXAMPLE 39

2,2-Bisfluoromethyl-6-trifluoromethyl-4-(2-oxo-1-piperidinyl)-2H-1-benzopyran (Compound 39)

Using trans-2,2-bisfluoromethyl-6-trifluoromethyl-3,4-dihydro-4-(2-oxo-1-piperindyl)-2H-1-benzopyran-3-ol as a starting material, 2,2-bisfluoromethyl-6-trifluoroemthyl-4-(2-oxo-1-piperidinyl)-2H-1-benzopyran represented by the following formula having a melting point of 166°–168° C. was obtained according to the same method as in Example 10.

NMR(CDCl$_3$)δ: 1.62–2.08(2H,m), 2.32–2.72(2H,m), 2.81–3.15(2H,m), 3.30–3.61(2H,m), 4.64(4H,dd), 5.63(1H, s), 6.81–7.26(2H,m), 7.40(1H,dd).

MS m/z: 361(M$^+$)

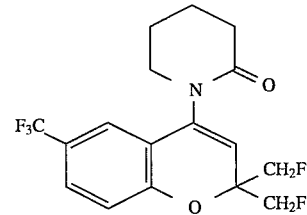

EXAMPLE 40

Trans-2,2-bisfluoromethyl-6-heptafluoropropyl-3,4-dihydro-4-(1,2-dihydro-2-oxo-1-pyridyl)-2H-1-benzopyran-3-ol (Compound 40)

Using 3,4-epoxy-2,2-bisfluoromethyl-6-heptafluoropropyl-3,4dihydro-2H-1-benzopyran as a starting material, trans-2,2-bisfluoromethyl-6-heptafluoropropyl-3,4-dihydro-4-(1,2-dihydro-2-oxo-1-pyridyl)-2H-1-benzopyran-3-ol represented by the following formula having a melting point of 111°–113° C. was obtained according to the same method as in Example 7.

NMR(CDCl₃)δ: 4.20–4.60(1H,m), 4.79(4H,d), 5.10–5.50(1H,m), 6.10–6.75(3H,m), 6.85–71.15(2H,m), 7.27(1H,dd), 7.40(1H,d), 7.51(1H,dd).

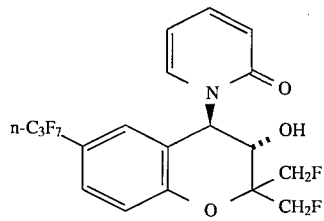

EXAMPLE 41

2,2-Bisfluoromethyl-6-heptafluoropropyl-4-(1,2-dihydro-2-oxo-1-pyridyl)-2H-1-benzopyran (Compound 41)

Using trans-2,2-bisfluoromethyl-6-heptafluoropropyl-3,4-dihydro-4-(1,2-dihydro-2-oxo-1-pyridyl)-2H-1-benzopyran-3-ol as a starting material, 2,2-bisfluoromethyl-6-heptafluoropropyl-4-(1,2-dihydro-2-oxo-1-pyridyl)-2H-1-benzopyran represented by the following formula having a melting point of 101°–104° C. was obtained according to the same method as in Example 10.

NMR(CDC₃)δ: 4.69(4H,d), 5.84(1H,s), 6.28(1H,dt), 6.64(1H,dd), 6.90(1H,d), 7.05(1H,d), 7.10–7.60(3H,m).

M/S m/z: 457(M⁺)

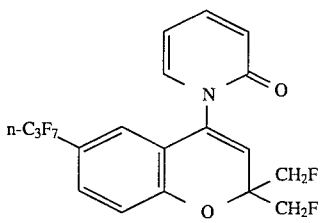

EXAMPLE 42

Trans-2,2-bisfluoromethyl-6-trifluoromethyl-3,4-dihydro-4-(1,2-dihydro-2-oxo-1-pyridyl)-2H-1-benzopyran-3-ol (Compound 42)

Using 3,4-epoxy-2,2-bisfluoromethyl-6-trifluoromethyl-3,4-dihydro-2H-1-benzopyran as a starting material, trans-2,2-bisfluoromethyl-6-trifluoromethyl-3,4-dihydro-4-(1,2-dihydro-2-oxo-1-pyridyl)-2H-1-benzopyran-3-ol represented by the following formula having a melting point of 210°–212° C. was obtained according to the same method as in Example 7.

270 MHz-NMR(CDCl₃)δ: 4.33(1H,d), 4.68–4.89(4H,m), 6.30(1H,t), 6.49(1H,d), 6.71(1H,d), 6.95(1H,d), 7.04(1H, bs), 7.16(1H,d), 7.40–7.47(2H,m), 7.53(1H,d).

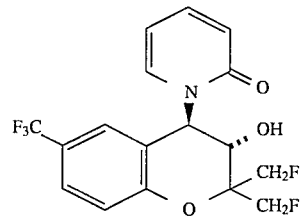

EXAMPLE 43

2,2-Bisfluoromethyl-6-trifluoromethyl-4-(1,2-dihydro-2-oxo-1-pyridyl)-2H-1-benzopyran (Compound 43)

Using trans-2,2-bisfluoromethyl-6-trifluoromethyl-3,4-dihydro-4-(1,2-dihydro-2-oxo-1-pyridyl)-2H-1-benzopyran-3-ol as a starting material, 2,2-bisfluoromethyl-6-trifluoromethyl-4-(1,2-dihydro-2-oxo-1-pyridyl)-2H-1-benzopyran represented by the following formula having a melting point of 139°–140° C. was obtained according to the same method as in Example 10.

NMR(CDCl₃)δ: 4.57(4H,d), 5.71(1H,s), 6.16(1H,dt), 6.51(1H,d), 6.71–7.02(2H,m), 7.06–7.50(3H,m).

MS m/z: 357(M⁺)

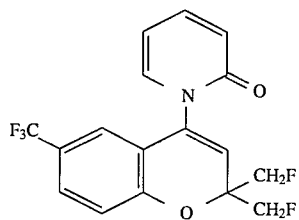

EXAMPLE 44

4-(2-Cyanoimino-1-pyrrolidinyl)-6-pentafluoroethyl-2,3-bisfluoromethyl-2H-1-benzopyran (Compound 44)

(1) Using 6-pentafluoroethyl-2,2-bisfluoromethyl-4-(2-oxo-1-pyrrolidinyl)-2H-1-benzopyran as a starting material, 6-pentaflurooethyl-2,2-bisfluroomethyl-4-(2-thioxo-1-pyrrolidinyl)-2H-1-benzopyran represented by the following formula having a melting point of 110°–112° C. was obtained according to the same method as in Example 13.

NMR(CDCl₃)δ: 1.95–2.57(2H,m), 3.17(2H,t), 3.84(2H,t), 4.59(4H,brd), 5.72(1H,s), 6.92(1H,d), 6.94(1H,d), 7.35(1H,dd).

MS m/z: 413(M⁺)

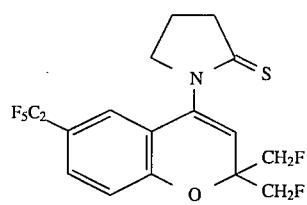

(2) To a mixture of 0.05 g of 6-pentafluoroethyl-2,2-bisfluoromethyl-4-(2-thioxo-1-pyrrolidinyl)-2H-1-benzopyran, 0.20 g of iodomethane, 0.05 g of cyanamide and 3 ml of tetrahydrofuran was added 0.06 g of sodium hydride (60%) under ice-cooling with stirring. The mixture was stirred under ice-cooling for 30 minutes and then stirred at room temperature for 17 hours. After addition of ice water, the mixture was extracted with methylene chloride. The organic layer was washed with water and dried. The solvent was distilled off and the resultant residue was purified using silica gel column chromatography (developing solution, MeOH:CH$_2$Cl$_2$=1:99) to obtain 49 mg of 4-(2-cyanoimino-1-pyrrolidinyl)-6-pentafluoroethyl-2,2-bisfluoromethyl-2H-1-benzopyran represented by the following formula having a melting point of 207°–210° C.

NMR(CDCl$_3$)δ: 2.14–2.60(2H,m), 3.13(2H,t), 3.80(2H,t), 4.55(2H,d), 4.60(2H,d), 5.76(1H,s), 6.86–7.13(2H,m), 7.45(1H,dd).

MS m/z: 421(M$^+$)

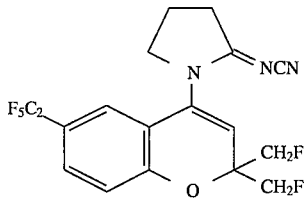

EXAMPLE 45

6-Pentafluoroethyl-2,2-bisfluoromethyl-4-(2-nitromethylene-1-pyrrolidinyl)-2H-1-benzopyran (Compound 45)

(1) To a mixture of 0.16 g of 6-pentafluoroethyl-2,2-bisfluoromethyl-4-(2-thioxo-1-pyrrolidinyl)-2H-1-benzopyran, 0.78 g of iodomethane, 0.41 g of nitromethane and 6 ml of tetrahydrofuran was added 0.10 g of sodium hydride (60%) at room temperature with stirring. The mixture was refluxed with heating for 2 hours. After addition of ice water, the mixture was extracted with methylene chloride. The organic layer was washed with water and dried. The solvent was distilled off and the resultant residue was purified using silica gel column chromatography (developing solution, MeOH:CH$_2$Cl$_2$=1:99) to obtain 0.02 g of 6-pentafluoroethyl-2,2-bisfluoromethyl-4-(2-nitromethylene-1-pyrrolidinyl)-2H-1-benzopyran represented by the following formula having a melting point of 195°–197° C.

NMR(CDCl$_3$)δ: 2.03–2.40(2H,m), 3.32–3.88(4H,m), 4.53(2H,d), 4.58(2H,d), 5.75(1H,s), 6.49(1H,s), 6.83–7.58(3H,m).

MS m/z: 440(M$^+$)

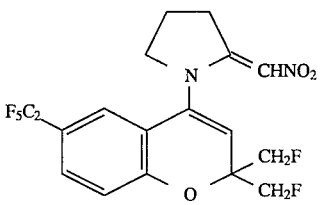

EXAMPLE 46

4-(2-Cyanoimino-1-piperidinyl)-6-pentafluoroethyl-2,2-bisfluoromethyl-2H-1-benzopyrin (Compound 46)

(1) Using 6-pentafluoroethyl-2,2-bisfluoromethyl-4-(2-oxo-1-pyrrolidinyl)-2H-1-benzopyran as a starting material, 6-pentafluoroethyl-2,2-bisfluoromethyl-4-(2-thioxo-1-piperidinyl)-2H-1-benzopyran represented by the following formula having a melting point of 118°–120° C. was obtained according to the same method as in Example 13.

NMR(CDCl$_3$)δ: 1.65–2.21(4H,m), 2.90–3.29(2H,m), 3.35–3.70(2H,m), 4.65(4H,brd), 5.65(1H,s), 6.98(1H,d), 7.00(1H,d), 7.41(1H,dd).

MS m/z: 427(M$^+$)

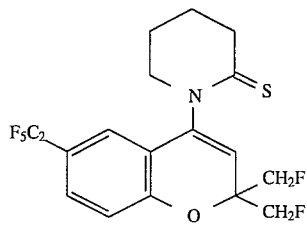

(2) Using 6-pentafluoroethyl-2,2-bisfluoromethyl-4-(2-thioxo-1-piperidinyl)-2H-1-benzopyran as a starting material, 4-(2-cyanoimino-1-piperidinyl)-6-pentafluoroethyl-2,2-bisfluoromethyl-2H-1-benzopyran represented by the following formula having a melting point of 196°–197° C. was obtained according to the same method as in Example 44.

NMR(CDCl$_3$)δ: 1.75–2.20(4H,m), 2.80–3.20(2H,m), 3.32–3.70(2H,m), 4.60(4H,brd), 5.70(1H,s), 6.89(1H,d), 7.01(1H,d), 7.44(1H,dd).

MS m/z: 435(M$^+$)

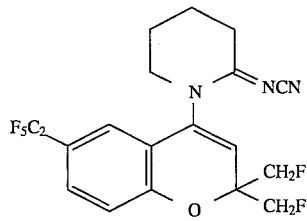

EXAMPLE 47

4-(2-Cyanoimino-1,2-dihydro-1-pyridyl)-6-pentafluoroethyl-2,2-bisfluoromethyl-2H-1-benzopyran (Compound 47)

(1) Using 6-pentafluoroethyl-2,2-bisfluoromethyl-4-(1,2-dihydro-2-oxo-1-pyridyl)-2H-1-benzopyran as a starting material, 6-pentafluoroethyl-2,2-bisfluoromethyl-4-(1,2-dihydro-2-thioxo-1-pyridyl)-2H-1-benzopyran represented by the following formula having a melting point of 122°–123° C. was obtained according to the same method as in Example 13.

NMR(CDCl$_3$)δ: 4.65(2H,d), 4.69(2H,d), 5.79(1H,s), 6.50–6.84(2H,m), 7.03(1H,d), 7.17–7.79(4H,m).

MS m/z: 423(M$^+$)

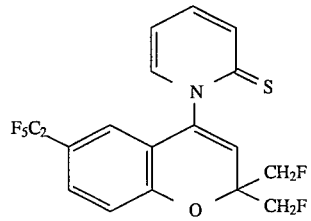

(2) Using 6-pentafluoroethyl-2,2-bisfluoromethyl-4-(1,2-dihydro-2-thioxo-1-pyridyl)-2H-1-benzopyran as a starting material, 4-(2-cyanoimino-1,2-dihydro-1-pyridyl)-6-pentafluoroethyl-2,2-bisfluoromethyl-2H-1-benzopyran represented by the following formula having a melting point of 196°–198° C. was obtained according to the same method as in Example 44.

NMR(CDCl$_3$)δ: 4.58(2H,d), 4.61(2H,d), 5.85(1H,s), 6.43–6.75(2H,m), 7.03(1H,d), 7.18–7.80(4H,m).

MS m/z: 431(M⁺)

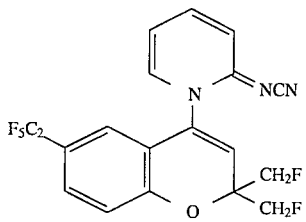

EXAMPLE 48

2-(6-Pentafluoroethyl-2,2-bisfluoromethyl-2H-1-benzopyran-4-yl)pyridine N-oxide (Compound 48)

(1) A mixture of 6.2 g of 2,2-bisfluoromethyl-6-nitro-4-(2-pyridyl)-2H-1-benzopyran, 11.7 g of stannous chloride and 80 ml of ethanol was refluxed with heating for 3 hours. The solvent was distilled off and sodium hydroxide solution was added to form an alkaline solution. The solution was extracted with methylene chloride and the organic layer was extracted with 2N hydrochloric acid. To the aqueous layer was added 2N sodium hydroxide to form a strongly alkaline solution, which was then extracted with methylene chloride. The organic layer was washed with water and dried and the solvent was distilled off to obtain 4.8 g of 6-amino-2,2-bisfluoromethyl-4-(2-pyridyl)-2H-1-benzopyran. To a mixture of 4.8 g of the above-obtained 6-amino-2,2-bisfluoromethyl-4-(2-pyridyl)-2H-1-benzopyran, 1.0 ml of concentrated sulfuric acid and 80 ml of water was added 1.20 g of sodium nitrite dissolved in 10 ml of water with stirring under ice-cooling. After the mixture was stirred for 20 minutes, 3.31 g of potassium iodide dissolved in 10 ml of water was added. After addition of 100 ml of methylene chloride, the mixture was stirred at room temperature for 2 hours. Water was added thereto and the mixture was extracted with methylene chloride. The organic layer was washed with sodium hydroxide solution and dried. The solvent was distilled off and the resultant residue was purified using silica gel column chromatography (developing solution, MeOH:CH₂Cl₂=1:99) to obtain 4.50 g of oily 2,2-bisfluoromethyl-6-iodo-4-(2-pyridyl)-2H-1-benzopyran represented by the following formula.

NMR(CDCl₃)δ: 4.56(4H,brd), 5.86(1H,s), 6.68(1H,brd), 7.09–7.88(5H,m), 8.62(1H,brd).

MS m/z: 399(M⁺)

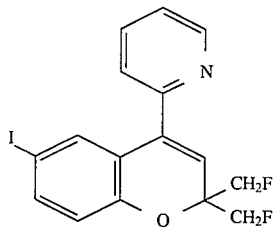

(2) A mixture of 1.11 g of 2,2-bisfluoromethyl-6-iodo-4-(2-pyridyl)-2H-1-benzopyran, 1.17 g of potassium pentafluoropropionate, 1.18 g of copper (I) iodide, 20 ml of N,N-dimethylformamide and 7.ml of toluene was stirred at 160° C. under nitrogen gas atmosphere with heating for 3 hours while toluene was distilled off. Ether and water were added thereto and the mixture was filtered using Celite. The mother liquor was extracted with ether. The organic layer was washed with water and dried. The solvent was distilled off and the resultant residue was purified using silica gel column chromatography (developing solution, MeOH:CH₂Cl₂=1:99) to obtain 0.86 g of oily 6-pentafluoroethyl-2,2-bisfluoromethyl-4-(2-pyridyl)-2H-1-benzopyran represented by the following formula.

NMR(CDCl₃)δ: 4.59(4H,brd), 5.90(1H,s), 6.98(1H,d), 7.08–7.82(5H,m), 8.59(1H,brd).

MS m/z: 391(M⁺)

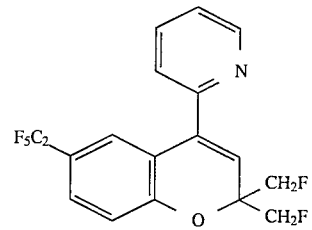

(3) To a mixture of 0.50 g of 6-pentafluoroethyl-2,2-bisfluoromethyl-4-(2-pyridyl)-2H-1-benzopyran and 15 ml of methylene chloride was added 0.70 g of m-chloroperbenzoic acid (70%) under ice-cooling with stirring. The mixture was stirred under ice-cooling for 1 hour and then stirred at room temperature for 16 hours. Potassium carbonate solution was added thereto and the mixture was extracted with methylene chloride. The organic layer was washed with water and dried. The solvent was distilled off and the resultant residue was purified using silica gel column chromatography (developing solution, MeOH:CH₂Cl₂=1:99) to obtain from the first eluted fraction 0.50 g of 2-(3,4-epoxy-6-pentafluoroethyl-2,2-bisfluoromethyl-3,4-dihydro-2H-1-benzopyran-4-yl)pyridine N-oxide represented by the following formula having a melting point of 125°–128° C.

NMR(CDCl₃)δ: 3.80(1H,s), 4.81(2H,d), 4.85(2H,d), 6.94(1H,d), 7.10(1H,d), 7.24–7.83(4H,m), 8.18–8.45(1H, m).

MS m/z: 423(M⁺)

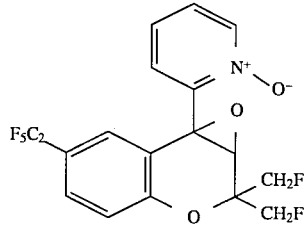

From the following eluted fraction, 0.04 g of 2-(6-pentafluoroethyl-2,2-bisfluoromethyl-2H-1-benzopyran-4-yl)pyridine N-oxide represented by the following formula having a melting point of 105°–107° C. was obtained.

NMR(CDCl₃)δ: 4.63(4H,d), 5.88(1H,s), 6.87(1H,d), 6.99(1H,d), 7.12–7.56(4H,m), 8.06–8.41(1H,m).

MS m/z: 407(M⁺)

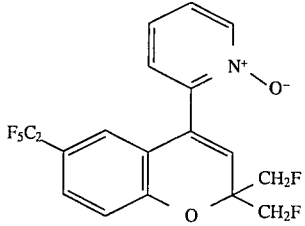

(4) A mixture of 0.50 g of 2-(3,4-epoxy-6-pentafluoroethyl-2,2-bisfluoromethyl-3,4-dihydro-2H-1-benzopyran-4-yl)pyridine N-oxide, 0.10 g of 10% palladium carbon and 15 ml of methanol was stirred at room temperature under hydrogen stream. The reaction mixture was subjected to vacuum filtration to remove the catalyst and the mother liquor was distilled off. The resultant residue was dissolved in 10 ml of dioxane and 0.82 g of soda talc was added thereto. The mixture was refluxed with heating for 1 hour and subjected to vacuum filtration to remove insoluble materials. Water was added to the mother liquor and the mixture was extracted with methylene chloride. The organic layer was washed with water and dried. The solvent was distilled off and the resultant residue was purified using silica gel column chromatography (developing solution, MeOH:CH$_2$Cl$_2$=1:99) to obtain 0.18 g of 2-(6-pentafluoroethyl-2,2-bisfluoromethyl-2H-1-benzopyran-4-yl)pyridine N-oxide.

EXAMPLE 49

2-(6-Pentafluoroethyl-2,2-bisfluoromethyl-2H-1-benzopyran-4-yl)pyridine N-oxide (Compound 49)

(1) To a mixture of 1.04 g of 2,2-bisfluoromethyl-6-iodo-4-(2-pyridyl)-2H-1-benzopyran and 20 ml of methylene chloride was added 0.78 g of m-chloroperbenzoic acid (70%) with stirring under ice-cooling. The mixture was stirred under ice-cooling for 1 hour and then stirred at room temperature for 25 hours. Potassium carbonate solution was added thereto and the mixture was extracted with methylene chloride. The organic layer was washed with water and dried. The solvent was distilled off and the resultant residue was purified using silica gel column chromatography (developing solution, MeOH:CH$_2$Cl$_2$=1:99) to obtain 0.25 g of oily 2-(2,2-bisfluoromethyl-6-iodo-2H-1-benzopyran-4-yl)pyridine N-oxide represented by the following formula.

NMR(CDCl$_3$)δ: 4.58(4H,brd), 5.80(1H,s), 6.65(1H,d), 6.92(1H,d), 7.17–7.57(4H,m), 8.10–8.40(1H,m).

MS m/z: 415(M$^+$)

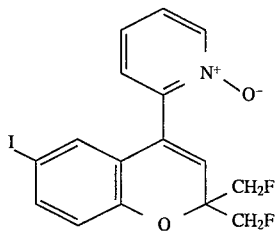

(2) Using 2-(2,2-bisfluoromethyl-6-iodo-2H-1-benzopyran-4-yl)pyridine N-oxide, 2-(6-pentafluoroethyl-2,2-bisfluoromethyl-2H-1-benzopyran-4-yl)pyridine N-oxide shown in Example 48 (3) was obtained according to the same method as in Example 48 (2).

EXAMPLE 50

2-(2,2-Bisfluoromethyl-6-trifluoromethyl-2H-1-benzopyran-4-yl)pyridine N-oxide (Compound 50)

(1) Using 2,2-bisfluoromethyl-6-iodo-4-(2-pyridyl)-2H-1-benzopyran and potassium trifluoroacetate, oily 2,2-bisfluoromethyl-6-trifluoromethyl-4-(2-pyridyl)-2H-1-benzopyran represented by the following formula was obtained according to the same method as in Example 48 (2).

NMR(CDCl$_3$)δ: 4.63(4H,d), 5.96(1H, s), 7.03(1H,d), 7.23–7.68(5H,m), 8.60–8.83(1H,m).

MS m/z: 341(M$^+$)

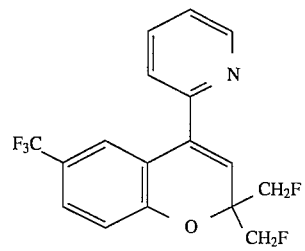

(2) Using 2,2-bisfluoromethyl-6-trifluoromethyl-4-(2-pyridyl)-2H-1-benzopyran, oily 2-(3,4-epoxy-2,2-bisfluoromethyl-6-trifluoromethyl-3,4-dihydro-2H-1-benzopyran-4-yl)pyridine N-oxide represented by the following formula was obtained according to the same method as in Example 48 (3).

NMR (CDCl$_3$)δ: 3.75(1H,s), 4.77(4H,d), 6.88–7.13(2H, m), 7.20–7.72(4H,m), 8.12–8.30(1H,m).

MS m/z: 373(M$^+$)

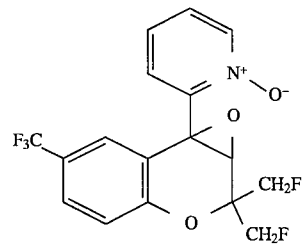

(3) Using 2-(3,4-epoxy-2,2-bisfluoromethyl-6-trifluoromethyl-3,4-dihydro-2H-1-benzopyran-4-yl)pyridine N-oxide, 2-(2,2-bisfluoromethyl-6-trifluoromethyl-2H-1-benzopyran-4-yl)pyridine N-oxide represented by the following formula having a melting point of 169°–170° C. was obtained according to the same method as in Example 48 (4).

270 MHz-NMR(CDCl$_3$)δ: 4.51–4.84(4H,m), 5.91(1H,s), 6.95(1H,d), 7.03(1H,d), 7.34–7.42(3H,m), 7.46(1H, dd), 8.32–8.35(1H,m).

MS m/z: 357(M$^+$)

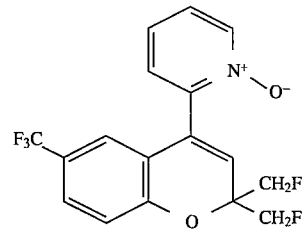

EXAMPLE 51

2-(2,2-Bisfluoromethyl-6-heptafluoropropyl-2H-1-benzopyran-4-yl)pyridine N-oxide (Compound 51)

(1) Using 2,2-bisfluoromethyl-6-iodo-4-(2-pyridyl)-2H-1-benzopyran and potassium heptafluorobutyrate, oily 2,2-bisfluoromethyl-6-heptafluoropropyl-4-(2-pyridyl)-2H-1-benzopyran represented by the following formula was obtained according to the same method as in Example 48 (2).

NMR (CDCl$_3$)δ: 4.68(4H,d), 6.05(1H,s), 7.11(1H,d), 7.33–8.00(5H,m), 8.55–9.00(1H,brs).

MS m/z: 441(M⁺)

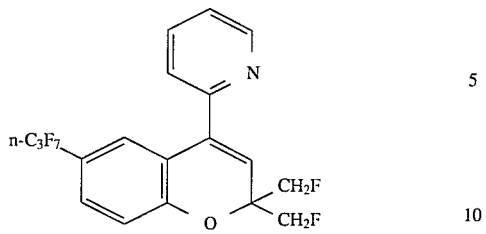

(2) Using 2,2-bisfluoromethyl-6-heptafluoropropyl-4-(2-pyridyl)-2H-1-benzopyran, oily 2-(2,2-bisfluoromethyl-6-heptafluoropropyl-2H-1-benzopyran-4-yl)pyridine N-oxide represented by the following formula was obtained according to the same method as in Example 28 (3).

270 MHz-NMR(CDCl₃)δ: 4.51–4.84(4H,m), 5.95(1H,s), 6.90(1H,d), 7.06(1H,d), 7.36–7.43(4H,m), 8.38–8.41(1H, m).

MS m/z: 457(M⁺)

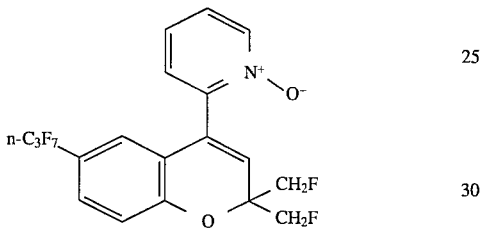

EXAMPLE 52

2-(2,2-Bisfluoromethyl-6-nitro-2H-1-benzopyran-4-yl)pyridine N-cyanoimine (Compound 52)

To a mixture of 200 mg of 2,2-bisfluoromethyl-6-nitro-4-(2-pyridyl)-2H-1-benzopyran and 2 ml of methylene chloride was added dropwise a mixture of 135 mg of (O-mesitylenesulfonyl)hydroxylamine and 3 ml of methylene chloride at room temperature with stirring. The mixture was stirred for 1 hour and ether was added thereto. The separated crystal was collected by filtration to obtain 240 mg of N-amino-2-(2,2-bisfluoromethyl-6-nitro-2H-1-benzopyran-4-yl)pyridinium mesitylenesulfonate. To a mixture of 60 mg of the above-obtained N-amino-2-(2,2-bisfluoromethyl-6-nitro-2H-1-benzopyran-4-yl)pyridinium mesitylenesulfonate and 1 ml of dimethylformamide was added 5 mg of sodium hydride and 36 mg of cyano bromide under ice-cooling with stirring. The mixture was stirred under ice-cooling for 1 hour. Water was added thereto and the mixture was extracted with ether. The organic layer was washed with water and dried. The solvent was distilled off and the resultant residue was purified using silica gel column chromatography (developing solution, MeOH:CH₂Cl₂=5:95) to obtain 11 mg of 2-(2,2-bisfluoromethyl-6-nitro-2H-1-benzopyran-4-yl)pyridine N-cyanoimine represented by the following formula having a melting point of 212°–214° C.

270 MHz-NMR(DMSO-d₆)δ: 4.58–4.92(4H,m), 6.22(1H,s), 7.20(1H,d), 7.38(1H,d), 7.75–7.83(1H,m), 7.89–7.97(2H,m), 8.13(1H,dd), 9.00–9.09(1H,m).

MS m/z: 358(M⁺)

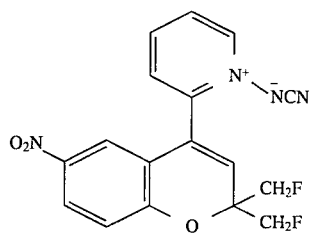

EXAMPLE 53

2-(6-Cyano-2,2-bisfluoromethyl-2H-1-benzopyran-4-yl)pyridine N-cyanoimine (Compound 53)

Using 6-cyano-2,2-bisfluoromethyl-4-(2-pyridyl)-2H-1-benzopyran as a starting material, 2-(6-cyano-2,2-bisfluoromethyl-2H-1-benzopyran-4-yl)pyridine N-cyanoimine represented by the following formula having a melting point of 251°–253° C. was obtained according to the same method as in Example 52.

270 MHz-NMR(DMSO-d₆)δ: 4.73(4H,brd), 6.11(1H, s), 7.12(1H,d), 7.28(1H,d), 7.66–7.91(4H,m), 8.96–8.99(1H, m).

MS m/z: 338(M⁺)

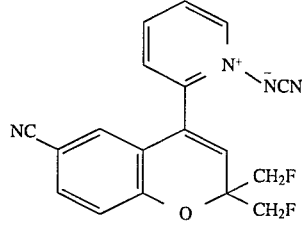

EXAMPLE 54

2-(2,2-Bisfluoromethyl-6-trifluoromethyl-2H-1-benzopyran-4-yl)pyridine N-cyanoimine (Compound 54)

Using 2,2-bisfluoromethyl-6-trifluoromethyl-4-(2-pyridyl)-2H-1-benzopyran as a starting material, 2-(2,2-bisfluoromethyl-6-trifluoromethyl-2H-1-benzopyran-4-yl)pyridine N-cyanoimine represented by the following formula having a melting point of 228°–230° C. was obtained according to the same method as in Example 52.

270 MHz-NMR(DMSO-d₆)δ: 4.61–4.88(4H,m), 6.12(1H,s), 6.88(1H,d), 7.16(1H,d), 7.59(1H,dd), 7.75–7.78(1H,m ), 7.88–7.91(2H,m), 9.00–9.03(1H,m).

MS m/z: 381(M⁺)

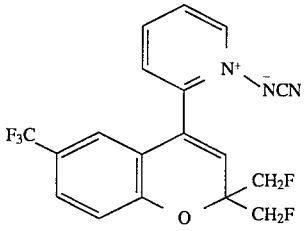

EXAMPLE 55

2-(6-Pentafluoroethyl-2,2-bisfluoromethyl-2H-1-benzopyran-4-yl)pyridine N-cyanoimine (Compound 55)

Using 6-pentafluoroethyl-2,2-bisfluoromethyl-4-(2-pyridyl)-2H-1-benzopyran as a starting material, 2-(6-pentafluoroethyl-2,2-bisfluoromethyl-2H-1-benzopyran-4-yl)pyridine N-cyanoimine represented by the following formula having a melting point of 190°–191° C. was obtained according to the same method as in Example 52.

270 MHz-NMR(DMSO-d$_6$)δ: 4.48–4.94(4H,m), 5.88(1H,s), 6.70(1H,d), 7.08(1H,d), 7.41–7.76(4H,m), 9.01–9.11(1H,m).

MS m/z: 431(M$^+$)

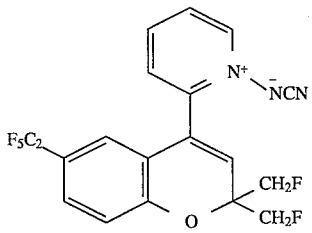

EXAMPLE 56

2-(2,2-Bisfluoromethyl-6-heptafluoropropyl-2H-1-benzopyran-4-yl)pyridine N-cyanoimine (Compound 56)

Using 2,2-bisfluoromethyl-6-heptafluoropropyl-4-(2-pyridyl)-2H-1-benzopyran as a starting material, 2-2,2 -bisfluoromethyl-6-heptafluoropropyl-2H-1-benzopyran-4-yl)pyridine N-cyanoimine represented by the following formula having a melting point of 162°–163° C. was obtained according to the same method as in Example 52.

NMR(CDCl$_3$)δ: 4.66(4H,d), 5.90(1H, s), 6.68(1H,d), 7.06(1H,d), 7.33–7.82(4H,m), 8.94–9.13(1H,m).

MS m/z: 481(M$^+$)

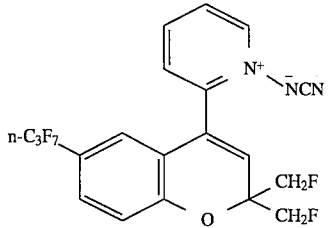

EXAMPLE 57

2-(2-Bisfluoromethyl-6-nitro-2H-1-benzopyran-4-yl)thiazole N-cyanoimine (Compound 57)

(1) A mixture of 3 g of 4-cyano-2,2-bisfluoromethyl-6-nitro-2H-1-benzopyran and 20 ml of sulfuric acid was stirred for 36 hours. The reaction mixture was poured into ice water and the separated crystal was collected by filtration. The above-obtained crystal was diluted with ethyl acetate and the organic layer was washed with water and dried. The solvent was distilled off to obtain 3 g of 2,2-bisfluoromethyl-6-nitro-2H-1-benzopyran-4-carboamide represented by the following formula.

NMR(CDCl$_3$-CD$_3$OD)δ: 4.59(4H,dd), 6.18(1H,s), 6.97(1H,d), 8.09(1H,dd), 8.46(1H,d).

MS m/z: 284(M$^+$)

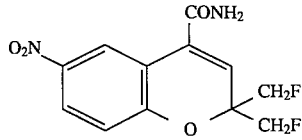

(2) Using 2,2-bisfluoromethyl-6-nitro-2H-1-benzopyran-4-carboamide as a starting material, 2,2-bisfluoromethyl-6-nitro-2H-1-benzopyran-4-carbothioamide represented by the following formula was obtained according to the same method as in Example 13.

NMR(CDCl$_3$-DMSO-d$_6$)δ: 4.64(4H,d), 5.92(1H,s), 7.03(1H,d), 8.09(1H,dd), 8.42(1H,d), 9.80(2H,brd).

MS m/z: 300(M$^+$)

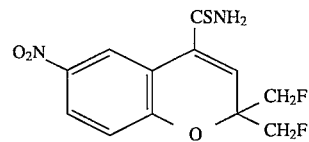

(3) A mixture of 600 mg of 2,2-bisfluoromethyl-6-nitro-2H-1-benzopyran-4-carbothioamide, 1.2 ml of bromoacetoaldehyde dimethylacetal, 11 mg of potassium hydroxide and 3 ml of benzene was refluxed with heating for 1 hour. Water was added thereto and the mixture was extracted with methylene chloride. The organic layer was washed with water and dried. The solvent was distilled off and the resultant residue was purified using silica gel column chromatography (developing solution, hexane:ethyl acetate=2:1) to obtain 380 mg of 2-(2,2-bisfluoromethyl-6-nitro-2H-1-benzopyran-4-yl)thiazol represented by the following formula.

NMR(CDCl$_3$)δ: 4.63 (4H,dd), 6.22(1H,s), 6.98(1H,d), 7.36(1H,d), 7.89(1H,d), 8.06(1H,dd), 8.96(1H,d).

MS m/z: 324(M$^+$)

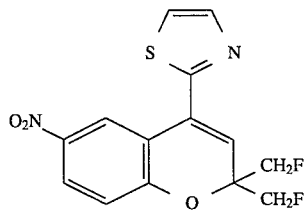

(4) Using 2-(2,2-bisfluoromethyl-6-nitro-2H-1-benzopyran-4-yl)thiazol as a starting material and potassium carbonate as a base instead of sodium hydride used in Example 52, 2-(2,2-bisfluoromethyl-6-nitro-2H-1-benzopyran-4-yl)thiazole N-cyanoimine represented by the following formula having a melting point of 193°–194° C. was obtained according to the same method as in Example 52.

270 MHz-NMR(DMSO-d$_6$)δ: 4.60–4.92(4H,m), 6.56(1H,s), 7.21(1H,d), 7.70(1H,d), 8.17(1H,dd), 8.31(1H, d), 8.53(1H,d).

MS m/z: 364(M$^+$)

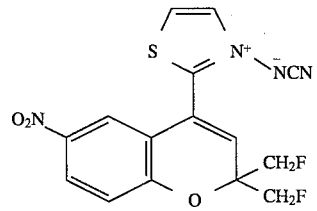

EXAMPLE 58

2,2-Bisfluoromethyl-6-nitro-4-(1-oxide-2-pyridyl)-2H-1,3-benzoxazine 3-oxide (Compound 58)

(1) To 1.0 g of 2,2-bisfluoromethyl-6-nitro-3,4-dihydro-2H-1,3-benzoxazin-4-one was added 50 ml of dichloromethane. To the mixture were added under ice-cooling 0.98 ml of trifluoromethanesulfonic anhydride and then 0.98 ml of 2,6-lutidine. The mixture was stirred for 23 hours. The solvent was distilled off and the resultant residue was purified using silica gel column chromatography (developing solution, CH₂Cl₂) to obtain 1.48 g of oily 4-trifluoromethanesulfonyloxy-2,2-bisfluoromethyl-6-nitro-2H-1,3-benzoxazine represented by the following formula.

NMR(CDCl₃)δ: 4.68(4H,d), 7.09(1H,d), 8.28(1H,d), 8.36(1H,dd).

MS m/z: 390(M⁺)

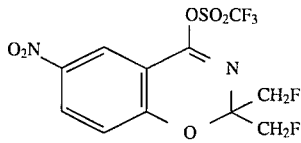

(2) To 3 ml of anhydrous tetrahydrofuran solution of 0.21 ml of 2-bromopyridine was added dropwise 1.38 ml of 1.68M n-butyllithium hexane solution at −78° C. under nitrogen atmosphere. After 30 minutes, 4.26 ml of solution of 0.5M zinc chloride in dry tetrahydrofuran was added thereto and the mixture was stirred at −78° C. for 15 minutes and under ice-cooling for 15 minutes. To the mixture were added under ice-cooling 65 mg of tetrakis(triphenylphosphine)palladium (0) and 330 mg of 4-trifluoromethanesulfonyloxy-2,2-bisfluoromethyl-6-nitro-2H-1,3-benzoxazine.

The mixture was warmed to room temperature and was stirred for additional 36 hours. Water was added to the reaction mixture which was then extracted with ethyl acetate and dried. The solvent was distilled off and the resultant residue was purified using column chromatography (developing solution, AcOEt:hexane=1:5) to obtain 110 mg of oily 2,2-bisfluoromethyl-6-nitro-4-(2-pyridyl)-2H-1,3-benzoxazine represented by the following formula.

NMR(CDCl₃)δ: 4.73(4H,d), 7.03(1H,d), 7.25–8.03(3H, m), 8.29(1H,dd), 8.68–8.85(1H,m), 9.00–9.13(1H,m).

MS m/z: 319(M⁺)

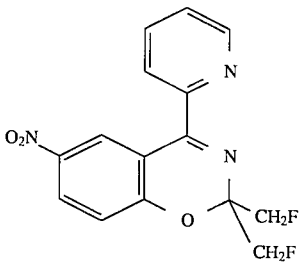

(3) In methylene chloride was dissolved 110 mg of 2,2-bisfluoromethyl-6-nitro-4-(2-pyridyl)-2H-1,3-benzoxazine. To the solution was added 116 mg of m-chloroperbenzoic acid (67%) under ice-cooling with stirring and the mixture was stirred at room temperature for 16 hours. Sodium bicarbonate solution was added thereto and the mixture was extracted with methylene chloride and dried. The solvent was distilled off and the resultant residue was purified using column chromatography (developing solution, MeOH:CH₂Cl₂=1:99) and recrystallized from a mixed solvent of ethyl acetate and hexane to obtain 9 mg of 2,2-bisfluoromethyl-6-nitro-4-(1-oxide-2-pyridyl)-2H-1,3-benzoxazine 3-oxide represented by the following formula having a melting point of 197°–200° C.

NMR(CDCl₃)δ: 4.78(4H,d), 7.06(1H,d), 7.43–7.54(3H, m), 7.84(1H,d), 8.27(1H,dd), 8.29–8.32(1H,m).

MS m/z: 351(M⁺)

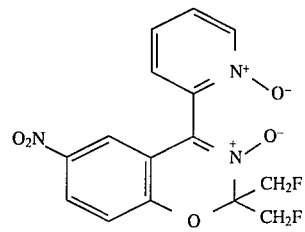

EXAMPLE 59

N-Acetylimino-2-(2,2-bisfluoromethyl-6-nitro-2H-1-benzopyran-4-yl)pyridine (Compound 59)

A mixture of 200 mg of N-amino-2-(2,2-bisfluoromethyl-6-nitro-2H-1-benzopyran-4-yl)pyridinium mesitylenesulfonate obtained in Example 52, 2 ml of acetic anhydride and 1 ml of acetyl chloride was stirred at 40° C. for hours. The mixture was concentrated under vacuum and diluted with methylene chloride. The mixture was washed with 10% sodium hydroxide solution and dried. The solvent was distilled off and the resultant residue was purified using silica gel column chromatography (developing solution, aq. NH₃:MeOH:CHCl₃=1:10:100) to obtain 96 mg of N-acetylimino-2-(2,2-bisfluoromethyl-6-nitro-2H-1-benzopyran-4-yl)pyridine represented by the following formula having a melting point of 202°–204° C.

NMR(CDCl₃)δ: 1.83(3H,s), 4.12–5.20(4H,m), 6.02(1H, s), 7.02(1H,d), 7.48–8.28(5H,m), 8.63(1H,dd).

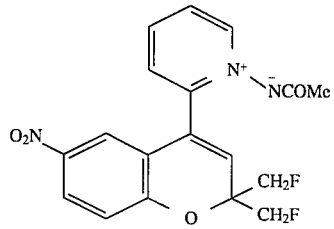

EXAMPLE 60

N-Methanesulfonylimino-2-(2,2-bisfluoromethyl-6-nitro-2H-1-benzopyran-4-yl)pyridine (Compound 60)

A mixture of 100 mg of N-amino-2-(2,2-bisfluoromethyl-6-nitro-2H-1-benzopyran-4-yl)pyridinium mesitylenesutfonate obtained in Example 52 and 2 ml of methanesulfonyl chloride was stirred at 40° C. for 3 hours. The mixture was poured into ice water and diluted with methylene chloride. The mixture was washed with 20% sodium hydroxide solution and dried. The solvent was distilled off and the resultant residue was purified using silica gel column chromatography (developing solution, MeOH:CH₂Cl₂=3:97) to obtain 20 mg of N-methanesulfonylimino-2-(2,2-bisfluoromethyl-6-nitro-2H-1-benzopyran-4-yl)pyridine represented by the following formula having a melting point of 197°–198° C.

270 MHz-NMR(DMSO-d₆)δ: 2.58(3H,s), 4.60–4.95(4H, m), 6.37(1H,s), 7.20(1H,d), 7.37(1H,d), 7.96–8.07(2H,m), 8.14(1H,dd), 8.30–8.38(1H,m), 9.01(1H,d).

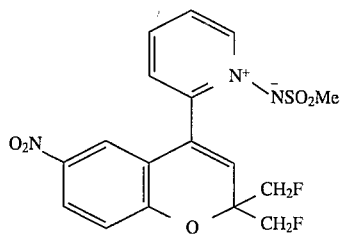

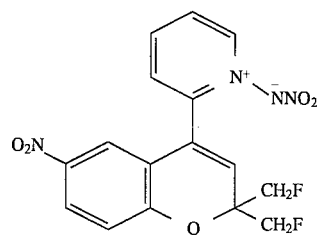

EXAMPLE 61

N-Benzoylimino-2-(2,2-bisfluoromethyl-6-nitro-2H-1-benzopyran-4-yl)pyridine (Compound 61)

To a mixture of 350 mg of N-amino-2-(2,2-bisfluoromethyl-6-nitro-2H-1-benzopyran-4-yl)pyridinium mesitylenesulfonate obtained in Example 52 and 1 ml of 20% sodium hydroxide solution was added 0.2 ml of benzoyl chloride under ice-cooling. The mixture was stirred at room temperature for 48 hours. The obtained product was collected by filtration and purified using silica gel column chromatography (developing solution, MeOH:CH$_2$Cl$_2$=5:95) to obtain 40 mg of N-benzoylimino-2-(2,2-bisfluoromethyl-6-nitro-2H-1-benzopyran-4-yl)pyridine represented by the following formula having a melting point of 189°–190° C.

NMR(CDCl$_3$)δ: 3.70–5.10(4H,m), 5.98(1H,s), 6.90(1H, d), 7.05–8.12(10H,m), 8.79(1H,dd).

EXAMPLE 63

N-Phenylcarbamoylimino-2-(2,2-bisfluoromethyl-6-nitro-2H-1-benzopyran-4-yl)pyridine (Compound 63)

To a mixture of 100 mg of N-amino-2-(2,2-bisfluoromethyl-6-nitro-2H-1-benzopyran-4-yl)pyridinium mesitylenesulfonate obtained in Example 52 and 4 ml of methylene chloride was added 0.03 ml of phenylisocyanate with stirring at room temperature. The mixture was stirred for 4 hours. Water was added thereto and the mixture was extracted with methylene chloride. The organic layer was washed with water and dried. The solvent was distilled off and the resultant residue was purified using silica gel column chromatography (developing solution, MeOH:CH$_2$Cl$_2$= 5:95) to obtain 40 mg of N-phenylcarbamoylimino-2-(2,2-bisfluoromethyl-6-nitro-2H-1-benzopyran-4-yl)pyridine represented by the following formula having a melting point of 103°–105° C.

270 MHz-NMR(acetone-d$_6$)δ: 4.45–4.96(4H,m), 6.18(1H,s), 6.71(1H,t), 6.95–7.18(3H,m), 7.22–7.48(3H,m), 7.59(1H,d), 7.81–8.19(4H, m), 9.11(1H,d).

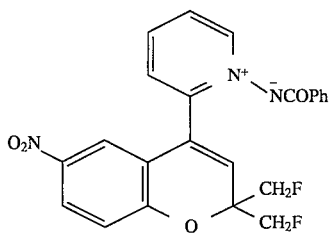

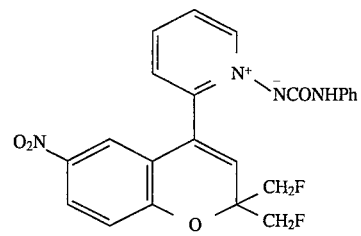

EXAMPLE 62

N-Nitroimino-2-(2,2-bisfluoromethyl-6-nitro-2H-1-benzopyran-4-yl)pyridine (Compound 62)

To a mixture of 200 mg of N-amino-2-(2,2-bisfluoromethyl-6-nitro-2H-1-benzopyran-4-yl)pyridinium mesitylenesulfonate obtained in Example 52, 1 ml of acetic anhydride and 0.5 ml of acetic acid was added under ice-cooling a mixture of 0.09 ml of nitric acid and 1 ml of acetic anhydride. The mixture was stirred at the same temperature for 2 hours. The mixture was concentrated under vacuum and diluted with methylene chloride. The mixture was washed with 10% sodium hydroxide solution and dried. The solvent was distilled off and the resultant residue was purified by recrystallization (recrystallization solvent: EtOH) to obtain 14 mg of N-nitroimino-2-(2,2-bisfluoromethyl-6-nitro-2H-1-benzopyran-4-yl)pyridine represented by the following formula having a melting point of 262°–264° C.

270 MHz-NMR(DMSO-d$_6$)δ: 4.50–4.90(4H,m), 6.22(1H, s), 7.22(1H,d), 7.45(1H,d), 8.14–8.30(3H,m), 8.66(1H,t), 9.10(1H,d).

EXAMPLE 64

6-Bromo-7-chloro-2,2-bisfluoromethyl-4-(1-oxide-2-pyridyl)-2H-1,3-benzoxazine 3-oxide (Compound 64)

(1) Using 1.60 g of 6-bromo-7-chloro-2,2-bisfluoromethyl-3,4-dihydro-2H-1,3-benzoxazin-4-one, 60 ml of methylene chloride, 1.61 ml of trifluoromethanesulfonic anhydride and 1.72 ml of 2,6-lutidine, 1.16 g of 6-bromo-7-chloro-4-trifluoromethanesulfonyloxy-2,2-bisfluoromethyl-2H-1,3-benzoxazine represented by the following formula was obtained according to the same method as in Example 58 (1).

NMR(CDCl$_3$)δ: 4.62(4H,d), 7.06(1H,s), 7.58(1H,s).
MS m/z: 457(M$^+$)

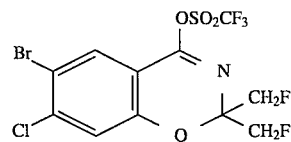

(2) Using 9 ml of dry tetrahydrofuran solution of 0.63 ml of 2-bromopyridine, 4.32 ml of 1.61M n-butyllithium hexane solution, 12.8 ml of solution of 0.5M zinc chloride dry tetrahydrofuran, 193 mg of tetrakis(triphenylphosphine- )palladium (0) and 1.16 g of 6-bromo-7-chloro-4-trifluoromethanesulfonyloxy-2,2-bisfluoromethyl-2H-1,3-benzoxazine, 230 mg of 6-bromo-7-chloro-2,2-bisfluoromethyl-4-(2-pyridyl)-2H-1,3-benzoxazine represented by the following formula was obtained according to the same method as in Example 58 (2).

NMR(acetone-$d_6$)δ: 4.73(4H,d), 7.08(1H, s), 7.31–7.60(1H,m), 7.76–8.00(2H, m), 8.41(1H,s), 8.51–8.68(1H,m).

MS m/z: 386($M^+$)

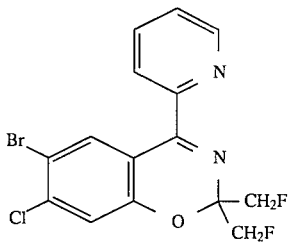

(3) Using 50 mg of 6-bromo-7-chloro-2,2-bisfluoromethyl-4-(2-pyridyl)-2H-1,3-benzoxazine and 32 mg of m-chloroperbenzoic acid (67%), 5 mg of 6-bromo-7-chloro-2,2-bisfluoromethyl-4-(1-oxide-2-pyridyl)-2H-1,3-benzoxazine 3-oxide represented by the following formula having a melting point of 146°–148° C. was obtained according to the same method as in Example 58 (3).

270 MHz-NMR(CDCl$_3$)δ: 4.74(4H,d), 7.10(1H,s), 7.18(1H,s), 7.39–7.48(3H,m), 8.27–8.30(1H,m).

MS m/z: 418($M^+$)

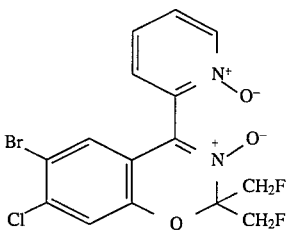

EXAMPLE 65

2-(2,2-Bistrifluoromethyl-6-nitro-2H-1-benzopyran-4-yl)pyridine N-oxide (Compound 65)

(1) Using 2,2-bistrifluoromethyl-3,4-dihydro-6-nitro-2H-1-benzopyran-4-one as a starting material, 4-trifluoromethanesulfonyloxy-2,2-bistrifluoromethyl-6-nitro-2H-1-benzopyran represented by the following formula having a melting point of 60°–61° C. was obtained according to the same method as in Example 28 (1).

NMR(CDCl$_3$)δ: 5.87(1H,s), 7.13(1H,d), 8.14–8.39(2H, m).

MS m/z: 461($M^+$)

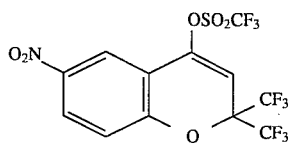

(2) To 5 ml of dry tetrahydrofuran solution 0 containing 0.16 ml of 2-bromopyridine was added dropwise 1.0 ml of 1.61M n-butyllithium hexane solution under nitrogen atmosphere at −78° C. After 30 minutes, 3.2 ml of solution of 0.5M zinc chloride in dry tetrahydrofuran was added thereto and the mixture was stirred at −78° C. for 15 minutes and under ice-cooling for 15 minutes. Then, the solution of 50 mg of tetrakis(triphenylphosphine)palladium (0) and 300 mg of 4-trifluoromethanesulfonyloxy-2,2-bistrifluoromethyl-6-nitro-2H-1-benzopyran dissolved in 5 ml of dry tetrahydrofuran was added under ice-cooling to the mixture obtained above. The resultant mixture was warmed to room temperature and stirred for additional 15 hours. Water was added to the reaction mixture which was then extracted with ethyl acetate. The organic layer was washed with water and dried. The solvent was distilled off and the resultant residue was purified using silica gel column chromatography (developing solution, CH$_2$Cl$_2$:hexane=1:1) to obtain 200 mg of 2,2-bistrifluoromethyl-6-nitro-4-(2-pyridyl)-2H-1-benzopyran represented by the following formula having a melting point of 105°–107° C.

NMR(CDCl$_3$)δ: 5.91(1H,s), 7.06(1H,d), 7.04–8.41(5H, m), 8.58–8.77(1H,m).

MS m/z: 390($M^+$)

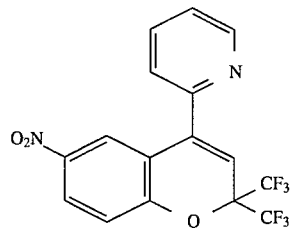

(3) In 4 ml of methylene chloride was dissolved 200 mg of 2,2-bistrifluoromethyl-6-nitro-4-(2-pyridyl)-2H-1-benzopyran and 210 mg of m-chloroperbenzoic acid (67%) was added thereto with stirring under ice-cooling. The mixture was stirred at room temperature for 14 hours. Potassium carbonate solution was added thereto and the mixture was extracted with methylene chloride. The organic layer was washed with water and dried. The solvent was distilled off and the resultant residue was purified using silica gel column chromatography (developing solution, MeOH:CH$_2$Cl$_2$=1:99) to obtain 140 mg of 2-(2,2-bistrifluoromethyl-6-nitro-2H-1-benzopyran-4-yl)pyridine N-oxide represented by the following formula having a melting point of 208°–210° C.

NMR(CDCl$_3$)δ: 5.96(1H,s), 7.15(1H,d), 7.33–7.60(3H, m), 8.16(1H,dd), 8.25–8.46(1H,m).

MS m/z: 406($M^+$)

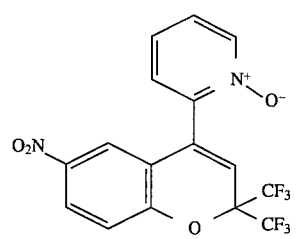

EXAMPLE 66

2-(6-Trifluoromethyl-2,2-bistrifluoromethyl-2H-1-benzopyran-4-yl)pyridine N-oxide (Compound 66)

(1) Using 2,2-bistrifluoromethyl-6-nitro-4-(2-pyridyl)-2H-1-benzopyran, oily 2,2-bistrifluoromethyl-6-iodo-4-(2-pyridyl)-2H-1-benzopyran represented by the following formula was obtained according to the same method as in Example 48 (1).

NMR(CDCl$_3$)δ: 5.74(1H,s), 6.66(1H,d), 7.06–7.80(5H, m), 8.45–8.68(1H,m).

MS m/z: 471(H⁺)

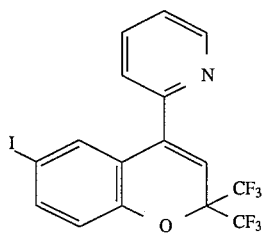

(2) Using 2,2-bistrifluoromethyl-6-iodo-4-(2-pyridyl)-2H-1-benzopyran and potassium trifluoroacetate, oily 6-trifluoromethyl-2,2-bistrifluoromethyl-4-(2-pyridyl)-2H-1-benzopyran represented by the following formula was obtained according to the same method as in Example 48 (2).

NMR(CDCl$_3$)δ: 5.81(1H,s), 7.00(1H,d), 7.01–7.90(5H, m), 8.52–8.73(1H,m).

MS m/z: 413(M⁺)

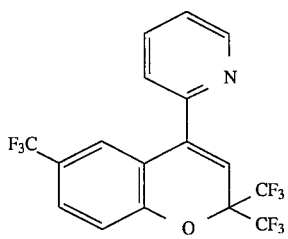

(3) Using 6-trifluoromethyl-2,2-bistrifluoromethyl-4-(2-pyridyl)-2H-1-benzopyran, oily 2-(6-trifluoromethyl-2,2-bistrifluoromethyl-2H-1-benzopyran-4-yl)pyridine N-oxide represented by the following formula was obtained according to the same method as in Example 65 (3).

NMR(CDCl$_3$)δ: 5.87(1H,s), 6.93–7.65(6H,m), 8.22–8.40(1H,m).

MS m/z: 429(M⁺)

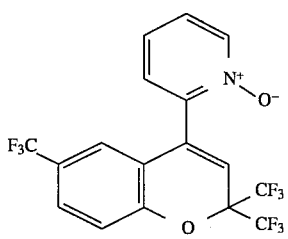

EXAMPLE 67

2-(6-Pentafluoroethyl-2,2-bistrifluoromethyl-2H-1-benzopyran-4-yl)pyridine N-oxide (Compound 67)

(1) Using 2,2-bistrifluoromethyl-6-iodo-4-(2-pyridyl)-2H-1-benzopyran and potassium pentafluororopionate, 6-pentafluoroethyl-2,2-bistrifluoromethyl-4-(2-pyridyl)-2H-1-benzopyran represented by the following formula having a melting point of 92°–93° C. was obtained according to the same method as in Example 48 (2).

NMR(CDCl$_3$)δ: 5.95(1H,s), 7.16(1H,d), 7.19–8.01(5H, m), 8.61–8.87(1H,m).

MS m/z: 463(M⁺)

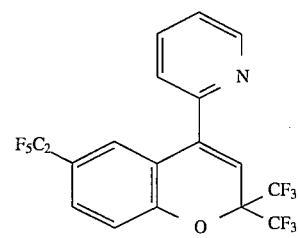

(2) Using 6-pentafluoroethyl-2,2-bistrifluoromethyl-4-(2-pyridyl)-2H-1-benzopyran, oily 2-(6-pentafluoroethyl-2,2-bistrifluoromethyl-2H-1-benzopyran-4-yl)pyridine N-oxide represented by the following formula was obtained according to the same method as in Example 65 (3).

NMR(CDCl$_3$)δ: 5.83(1H,s), 6.81–7.52(6H,m), 8.04–8.29(1H,m). MS m/z: 479(M⁺)

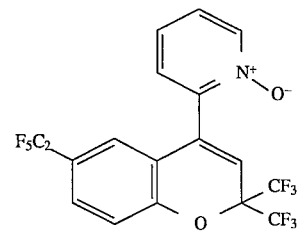

Excellent activities of the compound of the present invention on the K⁺ channel will now be demonstrated below by way of Test Examples.

Test Example 1

Test with Excised Aorta of Rat

The thoracic aorta was excised from a male Sprague Dawley rat (450 to 600 g) and cut into 2 mm wide ring preparations. Each preparation was suspended in 10 ml of an Organ bath containing a Krebs-Henseleit solution (NaCl:119; KCl:4.8; CaCl$_2$·2H$_2$O:2.53; KH$_2$PO$_4$:1.2; MgSO$_4$·7H$_2$O:1.2; NaHCO$_3$:24.8; glucose:10 (mM); 37° C.) under a tension of 2 g, and a mixed gas of 95% O$_2$ and 5% CO$_2$ was bubbled therethrough. Contraction reactions of the preparation were isometrically recorded by means of an FD pick-up. After equilibrium was reached in 1 to 1.5 hours, 30 mM KCl was added to cause a tissue contraction. The activity of a test compound to relax a lasting contraction by the addition of KCl was evaluated by obtaining a 50% inhibitory concentration (IC$_{50}$).

The compounds of the present invention obtained in the foregoing Examples and Cromakalim was used as test compound for comparison. The results obtained are shown in Table 1 below.

Test Example 2

Test with Guinea Pig Tracheal Muscle

The trachea was excised from a male Hartley guinea pig (450 to 550 g) to make chain preparations. The preparation was suspended in a bath containing the above-mentioned Krebs-henseleit solution (37° C.) through which a mixed gas of 95% O$_2$ and 5% CO$_2$ was bubbled. Contraction reactions of the preparation were isometrically recorded under a tension of 1 g. The relaxing activity of 1 mM aminophylline on spontaneous tension being taken as 100%, a concentration of a test compound exhibiting 50% relaxing activity (IC$_{50}$) was obtained.

The same test compound as used in Text Example 1 were used. The results obtained are shown in Table 1.

TABLE 1

| Compound No. | Rat Aorta $IC_{50}$ (M) | Guinea Pig Tracheal Muscle $IC_{50}$ (M) |
|---|---|---|
| 2-2 | $7.4 \times 10^{-8}$ | $3.9 \times 10^{-7}$ |
| 6-2 | $2.6 \times 10^{-9}$ | $6.8 \times 10^{-9}$ |
| 4-2 | $2.8 \times 10^{-10}$ | $6.9 \times 10^{-9}$ |
| 12 | $2.5 \times 10^{-9}$ | $5.9 \times 10^{-9}$ |
| 48 | $1.6 \times 10^{-9}$ | $3.9 \times 10^{-9}$ |
| 50 | $5.1 \times 10^{-9}$ | $1.8 \times 10^{-8}$ |
| 52 | $2.0 \times 10^{-9}$ | $1.2 \times 10^{-8}$ |
| 55 | $8.2 \times 10^{-10}$ | $6.3 \times 10^{-9}$ |
| Cromakalim | $1.7 \times 10^{-7}$ | $8.6 \times 10^{-7}$ |

[Industrial Applicability]

The compounds of the present invention have excellent $K^+$ channel opening activity and are therefore expected to make great contribution to the art, such as medical composition utilizing $K^+$ channel opening activating (e.g., anti-asthmatics).

We claim:

1. A compound represented by the formula:

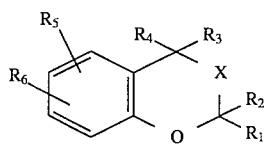

wherein $R_1$ and $R_2$ are $CH_2F$, $R_3$ represents a hydrogen atom or is directly bonded to X to represent a single bond, $R_4$ represents

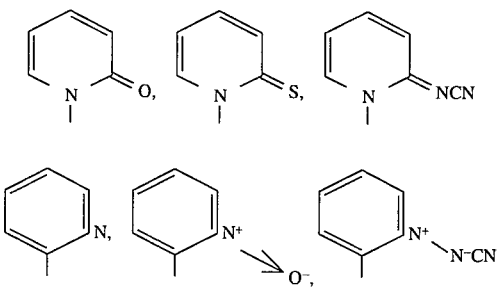

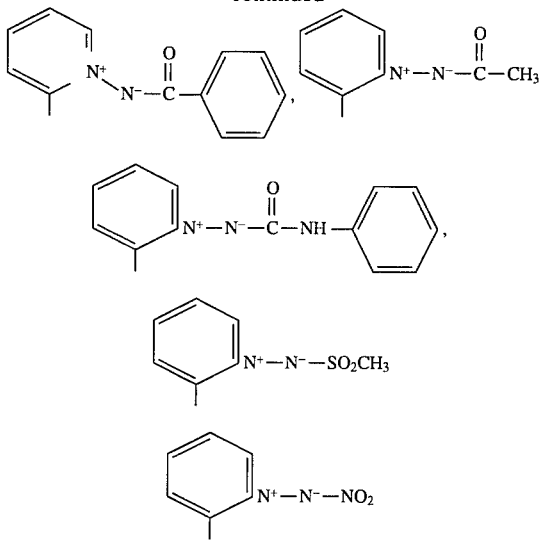

$R_5$ and $R_6$, which may be the same or different, represent a hydrogen atom, a halogen, a lower alkyl group, a lower haloalkyl group, a nitro group or a cyano group, X represents

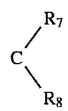

wherein $R_7$ and $R_8$, which may be the same or different, represent a hydrogen atom, a hydroxyl group or a lower acyloxy group, or $R_7$ is directly bonded to $R_3$ to represent a single bond.

2. 6-pentafluoroethyl-2,2-bisfluoromethyl-4-(1,2-dihydro-2-oxo-1-pyridyl)-2H-1-benzopyran.

3. A $K^+$ channel activator comprising 6-pentafluoroethyl-2,2-bisfluoromethyl-4-(1,2-dihydro-2-oxo-1-pyridyl)-2H-1-benzopyran and a pharmaceutically acceptable carrier.

* * * * *

UNITED STATES PATENT AND TRADEMARK OFFICE
CERTIFICATE OF CORRECTION

PATENT NO. : 5,614,633
DATED : Mar. 25, 1997
INVENTOR(S) : Koga et al.

It is certified that error appears in the above-indentified patent and that said Letters Patent is hereby corrected as shown below:

Cover item, line [22], delete "Mar. 15, 1995" and insert therefor --August 17, 1993--.

Signed and Sealed this

Thirtieth Day of September, 1997

Attest:

BRUCE LEHMAN

Attesting Officer

Commissioner of Patents and Trademarks